US012746272B2

(12) United States Patent
Williams

(10) Patent No.: US 12,746,272 B2
(45) Date of Patent: Sep. 29, 2026

(54) METHOD OF TREATMENT OF CANCER OR TUMOUR

(71) Applicant: USWM CT, LLC, Louisville, KY (US)

(72) Inventor: Dennis Robert Williams, Abingdon (GB)

( * ) Notice: Subject to any disclaimer, the term of this patent is extended or adjusted under 35 U.S.C. 154(b) by 905 days.

(21) Appl. No.: 17/924,982

(22) PCT Filed: May 13, 2021

(86) PCT No.: PCT/GB2021/051157
§ 371 (c)(1),
(2) Date: Jan. 23, 2023

(87) PCT Pub. No.: WO2021/229234
PCT Pub. Date: Nov. 18, 2021

(65) Prior Publication Data

US 2023/0190803 A1 Jun. 22, 2023

Related U.S. Application Data

(60) Provisional application No. 63/089,611, filed on Oct. 9, 2020, provisional application No. 63/030,503, filed on May 27, 2020, provisional application No. 63/024,077, filed on May 13, 2020.

(51) Int. Cl.

| | |
|---|---|
| ***A61K 38/17*** | (2006.01) |
| ***A61K 40/11*** | (2025.01) |
| ***A61K 40/32*** | (2025.01) |
| ***A61K 40/42*** | (2025.01) |
| ***A61P 11/00*** | (2006.01) |
| ***A61P 25/00*** | (2006.01) |
| ***A61P 35/00*** | (2006.01) |
| ***A61P 35/04*** | (2006.01) |
| *A61K 39/00* | (2006.01) |
| *C12N 5/0783* | (2010.01) |

(52) U.S. Cl.
CPC ........ *A61K 38/177* (2013.01); *A61K 38/1774* (2013.01); *A61K 40/11* (2025.01); *A61K 40/32* (2025.01); *A61K 40/4268* (2025.01); *A61P 11/00* (2018.01); *A61P 25/00* (2018.01); *A61P 35/00* (2018.01); *A61P 35/04* (2018.01); *A61K 2039/5154* (2013.01); *A61K 2039/545* (2013.01); *C12N 5/0636* (2013.01)

(58) Field of Classification Search
CPC .................................................... A61K 38/177
USPC ....................................................... 424/154.1
See application file for complete search history.

(56) References Cited

U.S. PATENT DOCUMENTS

2022/0370559 A1* 11/2022 Silk .................... A61K 38/1774

FOREIGN PATENT DOCUMENTS

| | | | |
|---|---|---|---|
| JP | 2019528748 | A | 10/2019 |
| WO | 2018055140 | A1 | 3/2018 |
| WO | WO 2020/109616 | A1 | 6/2020 |
| WO | WO 2021/144338 | A1 | 7/2021 |

OTHER PUBLICATIONS

Klebanoff et al (TRENDS in Immunology, 2005, 26(2): 111-117).*
Turtle et al (Blood, 2015, 126(23): 3773).*
International Search Report for PCT/GB2021/051157 dated Sep. 14, 2021, 7 pages.
Written Opinion of the International Searching Authority for PCT/GB2021/051157 dated Sep. 14, 2021, 6 pages.
Robbins et al., "Single and Dual Amino Acid Substitutions in TCR CDRs Can Enhance Antigen-Specific T Cell Functions", The Journal of Immunology; (2008) vol. 180, No. 9, pp. 6116-6131.
San Miguel et al., "Engineering Anti-myeloma Responses Using Affinity-Enhanced TCR-Engineered T Cells", Cancer Cell; (2015) 28 (3), pp. 281-283.
Schmitt et al., "Enhanced-affinity murine T-cell receptors for tumor/self-antigens can be safe in gene therapy despite surpassing the threshold for thymic selection", Blood; (2013) vol. 122, pp. 348-356.
Jiang et al., "DDX3X Is the Most Frequently Mutated Gene in Natural Killer/T-cell Lymphoma", Cancer Discovery; (2015) 5, p. 901.
Needleman et al., "A General Method Applicable to the Search for Similarities in the Amino Acid Sequence of Two Proteins," Journal of Molecular Biology; (1970) vol. 48, pp. 443-453.
Altschul et al., "Basic Local Alignment Search Tool," Journal of Molecular Biology; (1990) vol. 215, pp. 403-410.
Pearson et al., "Improved tools for biological sequence comparison," Proceedings of the National Academy of Sciences; (1988) vol. 85, pp. 2444-2448.
Smith et al., "Identification of Common Molecular Subsequences," Journal of Molecular Biology; (1981) vol. 147, pp. 195-197.
Eisenhauer et al., "New response evaluation criteria in solid tumours: Revised RECIST guideline (version 1.1)," European Journal of Cancer; ( 2009 ) vol. 45, pp. 228-247.
Sanderson et al., "Preclinical evaluation of an affinity-enhanced MAGE-A4-specific T-cell receptor for adoptive T-cell therapy," OncoImmunology; Nov. 24, 2019, vol. 9, No. 1, e1682381, 11 pages.
Anderson et al., "Abstract 2313: Enhanced activity of second-generation MAGE-A4 Spear T-cells through co-expression of a CD8 [alpha] homodimer," Cancer Research; Jul. 1, 2019, vol. 79, No. 13S, A2313, 2 pages.
Hong et al., "Initial safety assessment of MAGE-A4 Spear T-cells," Annals of Oncology; Oct. 2018, vol. 29, No. S8, p. viii412.
Van Tine et al., "ADP-A2M4 (MAGE-A4) in patients with synovial sarcoma," Annals of Oncology; Oct. 2019, vol. 30, No. S5, pp. v684-v685.

(Continued)

*Primary Examiner* — Sean E Aeder
(74) *Attorney, Agent, or Firm* — Grimes & Yvon LLP

(57) ABSTRACT

The present invention relates to a method of treating, preventing or delaying the progression of cancer and/or tumour in a subject comprising administering to the subject a treatment regimen comprising an effective amount of modified immunoresponsive cells expressing or presenting a heterologous T-cell receptor (TCR) having the property of binding to MAGE A4.

21 Claims, 8 Drawing Sheets

Figure 2:
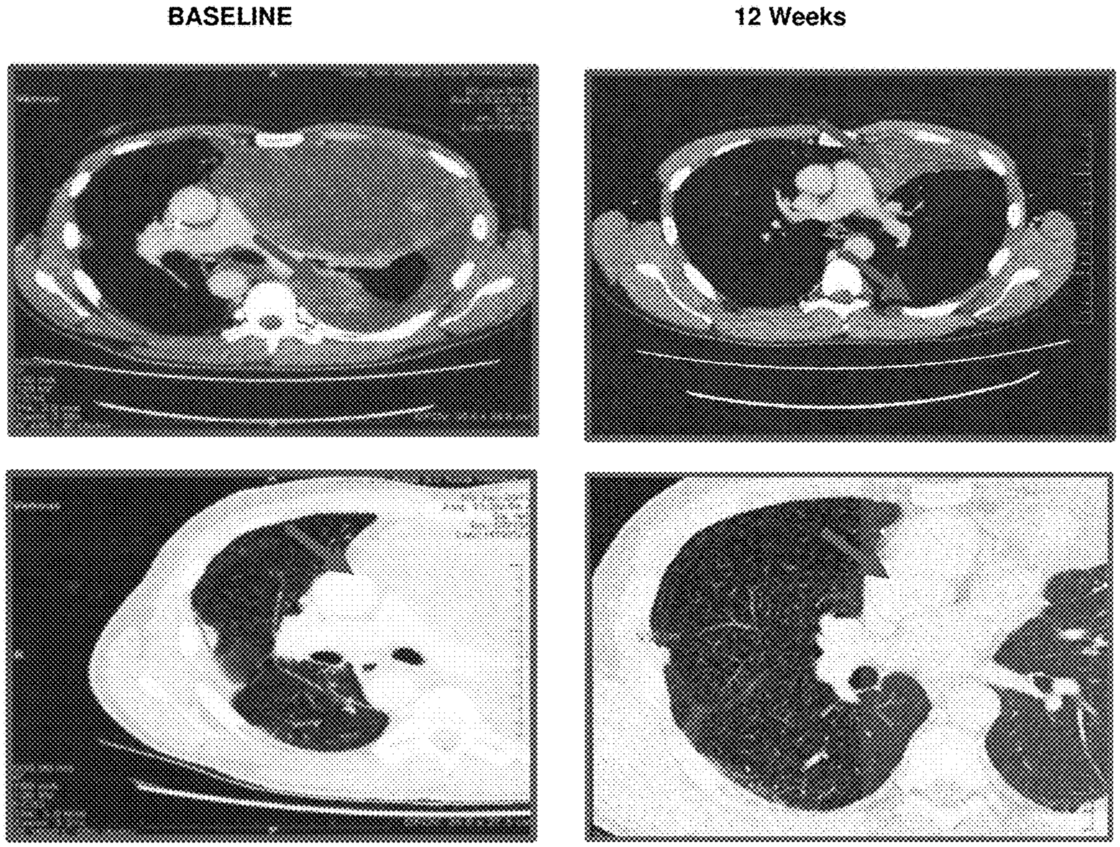

Specification includes a Sequence Listing.

(56) References Cited

OTHER PUBLICATIONS

Doroshow et al., "Immunotherapy in Non-Small Cell Lung Cancer: Facts and Hopes," Clinical Cancer Research; Aug. 1, 2019, vol. 25, No. 15, pp. 4592-4602.
Cramer et al., "Immunotherapy for head and neck cancer: Recent advances and future directions," Oral Oncology; Dec. 1, 2019, vol. 99, 104460, 20 pages.
Goode et al. "Immunotherapy for Gastroesophageal Cancer," Journal of Clinical Medicine 2016, 5, 84, pp. 1-14.

* cited by examiner

Figure 1.

| | Head and Neck Cancer | Lung Cancer |
|---|---|---|
| Number of subjects | 3 | 2 |
| BOR partial response (%) | 1 (33.3) | 1 (50.0) |
| BOR stable disease (%) | 1 (33.3) | 1 (50.0) |
| BOR progressive disease (%) | 1 (33.3) | 1 (50.0) |
| Unknown / missing (%) | | |
| ORR (%) | 33.3 | 50.0 |
| | | |
| | | |

Figure 3

| Cancer | % change reduction from baseline lesion SLC | Weeks after MAGE-A4$^{c1032}$ T-cell infusion |
|---|---|---|
| Head and Neck | 36 | 24 |
| Lung | 36 | 16 |
| Lung | 41 | 20 |
| Ovarian | 9 | 12 |
| Melanoma | 21 | 6 |
| Urothelial / Bladder | 67 | 6 |
| | | |

Percent changes in sum of diameters in target lesions measurement (Sum of Diameters = Sum of the long diameters for non-nodal lesions and short axis for nodal lesions), responses evaluated by RECIST v1.1

Progression Free Survival

(median PFS is ~ 20 weeks, i.e. >= 20 weeks)

Overall Survival

(median OS is not reached)

Figure 5

| | Synovial Sarcoma |
|---|---|
| Number of subjects | 16 |
| BOR partial response (%) | 7 (43.8) |
| BOR stable disease (%) | 7 (43.8) |
| BOR progressive disease (%) | 1 (6.3) |
| Unknown / missing (%) | 1 (6.3) |
| ORR (%) | 43.8 |
| | |
| | |

Figure 6A

| Treatment | Response Rate % |
| --- | --- |
| Pazopanib | 4 |
| Trabectedin | 7 |
| Eribulin | 4 |
| Gemcitabine +/- Docetaxel | 8-16 |
| Dacarbazine | 4-6 |

Figure 6B

| Treatment | Overall Response Rate % |
| --- | --- |
| MAGE-A4$^{c1032}$ T-cell infusion | 46.6% (95% CI: 21.27, 73.41) |

Row A = Target lesion 1 - Right paratracheal lymph node

Row B = Target lesion 2 - Subcarinal lymph node

BASELINE WEEK 20

Right Adrenal Metastasis - 6.7

Right Adrenal Metastasis - 3.5

Tabulated Data for Subject (subject of above CT scans)

| | BSL | Week 6 | Week 12 | Week 16 | Week 20 |
|---|---|---|---|---|---|
| target Lesion (mm) | 108 | 88 | 72 | 69 | 63 |
| change from BSL | | -18.5% | -33.3% | -36.1% | -41.7% |
| assessment | | SD | PR | PR | PR |

SD = stable disease, PR = partial response

METHOD OF TREATMENT OF CANCER OR TUMOUR

FIELD OF INVENTION

The present invention relates to a method of treating, preventing or delaying the progression of cancer and/or tumour in a subject comprising administering to the subject a treatment regimen comprising an effective amount of modified immunoresponsive cells expressing or presenting a heterologous T-cell receptor (TCR) having the property of binding to MAGE A4 or antigenic peptide thereof, in particular the treatment of Head and Neck Cancer or Lung Cancer.

BACKGROUND

Head and neck cancer therapy: Head and neck cancer is a group of cancers affecting the mouth, nose, throat, larynx, sinuses, or salivary glands and are in the majority squamous cell cancers. Together, these cancers are the seventh most-frequent cancer and the ninth most-frequent cause of death from cancer and they globally affect more than 5.5 million people.

The cancer is strongly linked to tobacco and alcohol use although other known risk factors are viral in origin and include Epstein-Barr virus or human papillomavirus infections. The mutational profile of HPV+ and HPV− head and neck cancer demonstrates that these are fundamentally distinct cancers.

Head and neck cancer commonly affects individuals of between 55 and 65 years old, males are affected twice as often as females. The average 5-year survival following diagnosis is 42-64%, early-stage oral cancers have improved cure rates, however the majority of patients present with more advanced cancer which is less easily treated. A significant percentage of patients following first line success proceed to develop second primary tumors at a rate of 9% to 23% at 20 years, often due to the same carcinogenic exposure responsible for the original tumour. Diagnosis is staged according to the TNM classification system, where T is the size and configuration of the tumor, N is the presence or absence of lymph node metastases, and M is the presence or absence of distant metastases. The T, N, and M characteristics are combined to produce a "stage" of the cancer, from I to IVB. Surgical resection and radiation therapy (including 3D conformal radiation therapy, intensity-modulated radiation therapy, particle beam therapy and brachytherapy,) or concomitant chemotherapy regimens are the main course of treatment for most head and neck cancers as the standard of care for tumour with regional metastases (stage III or IV), surgery alone may suffice for early primary cancers without regional metastases (stage I or II). Typical chemotherapy agents are a combination of paclitaxel and carboplatin, docetaxel is also an approved treatment for advanced head and neck cancer, either alone or in combination with cisplatin and/or fluorouracil. Immune checkpoint blockade also offer further therapy options, pembrolizumab is approved for first-line treatment of metastatic or unresectable recurrent HNSCC or nivolumab, approved for the treatment of recurrent or metastatic HNSCC with disease progression on or after platinum-based chemotherapy. Some targeted antibody therapy options for squamous cell cancers of the head and neck include cetuximab, bevacizumab and erlotinib, including combination of cetuximab with conventional chemotherapy cisplatin. Cetuximab and platin/5-fluorouracil is a recognised first-line regimen.

Where the head and neck cancer affects the throat or throat cancer is near the bottom of the throat, it has a high likelihood of spreading to the lungs.

Lung cancer therapy: Lung cancer is the most common cause of cancer-related death in men and second most common in women after breast cancer, in the United States, the five-year survival rate is around 20%. It originates from environmental carcinogens due to tobacco smoking, chemical agent or asbestos exposure, and air pollution which cause genetic damage to DNA and epigenetic changes this may also be combined with genetic factors of predisposition. About 8% of lung cancer is related to inherited factors. The condition is commonly treated by surgery (resection), chemotherapy, and radiotherapy. For early-stage non-small cell lung cancer NSCLC, removal of a lobe of lung (lobectomy) is the surgical treatment of choice, for small cell lung cancer SCLC, chemotherapy and/or radiotherapy is typically used.

In advanced NSCLC, chemotherapy is used as first-line treatment and sometimes second line. Typically, two drugs are used, of which one is often platinum-based (either cisplatin or carboplatin). Other commonly used drugs are gemcitabine, paclitaxel, nab-paclitaxel docetaxel, pemetrexed, etoposide or vinorelbine. A combination of vinorelbine and cisplatin is used in the adjuvant setting. In SCLC, cisplatin and etoposide are most commonly used. Combinations with carboplatin, gemcitabine, paclitaxel, vinorelbine, topotecan, and irinotecan are also sometimes used. Radiotherapy is often given together with chemotherapy, and may be used with curative intent in people with NSCLC who are not eligible for surgery and for potentially curable SCLC. Targeted therapy is of increasing importance for advanced lung cancer for example in for both SCLC and NSCLC, e.g. tyrosine kinase inhibitors and epidermal growth factor receptor (EGFR) inhibitors such as erlotinib, gefitinib and afatinib (e.g. for EGFR mutation or EGFR M+ lung cancer) or Denosumab monoclonal antibody against receptor activator of nuclear factor kappa-B ligand.

It is desirable therefore to provide a therapy for tumour and/or cancer treatment, such as treatment of head and neck cancer or lung cancer and/or tumour, which is cancer specific, capable of treating intermediate or late stage cancer or single or multiple solid tumours, particularly where there has been failure or recurrence following primary therapy or surgery, preferably also where the therapy minimises or reduces toxicity or side effects for example risk of systemic toxicity of chemotherapeutic agents (e.g. nausea, vomiting, anaemia, and thrombocytopenia) or tissue damage due to radiotherapy.

The present invention relates to and exemplifies the treatment of head and neck or lung cancer and/or tumour in a subject comprising administering to the subject a treatment regimen comprising an effective amount of modified T-cells expressing or presenting a heterologous T-cell receptor (TCR) having the property of binding to MAGE A4 and in particular, specifically binding to GVYDGREHTV, SEQ ID NO: 2. In particular, the HLA-A2 restricted MAGE A4 peptide GVYDGREHTV, SEQ ID NO: 2, which provides a suitable target for novel immunotherapeutic interventions; this peptide is naturally processed and has been isolated from head and neck and lung carcinoma lines.

SUMMARY OF THE INVENTION

According to a first aspect of the present invention there is provided a method of treating, preventing or delaying the progression of head and neck or lung cancer and/or tumour in a subject comprising administering to the subject a treatment regimen comprising an effective amount of modified immunoresponsive cells expressing or presenting a heterologous T-cell receptor (TCR) or chimeric antigen receptor (CAR) binding to MAGE A4 or a MAGE A4 antigenic peptide thereof.

According to the invention the TCR or CAR may bind MAGE A4, or an antigenic peptide thereof, for example Human MAGE A4 or MAGE A4 of SEQ ID NO: 1 or an antigenic peptide thereof. The TCR or CAR may bind to an antigenic peptide comprising SEQ ID NO: 2, GVYDGREHTV.

The invention moreover provides a modified immunoresponsive cell expressing or presenting a heterologous T-cell receptor (TCR) or chimeric antigen receptor (CAR) binding to MAGE A4 or a MAGE A4 antigenic peptide thereof for use in treating, preventing or delaying the progression of cancer and/or tumour in a subject.

In embodiments, the heterologous T-cell receptor (TCR) is a TCR which binds a peptide antigen of MAGE A4 comprising GVYDGREHTV, SEQ ID NO: 2.

In certain embodiments, the use according to the invention comprises administering to the subject a treatment regimen comprising an effective amount of the modified immunoresponsive cells expressing or presenting a heterologous T-cell receptor (TCR).

Immunoresponsive Cells

According to the present invention the modified immunoresponsive cells can be cells of the lymphoid lineage, comprising B, T or natural killer (NK) cells. The modified immunoresponsive cells may be cells of the lymphoid lineage including T cells, Natural Killer T (NKT) cells, and precursors thereof including embryonic stem cells, and pluripotent stem cells (e.g, those from which lymphoid cells may be differentiated). T cells can be lymphocytes that mature in the thymus and are chiefly responsible for cell-mediated immunity and also involved in the adaptive immune system. According to the present invention the T cells can include, but are not limited to, helper T cells, cytotoxic T cells, memory T cells (including central memory T cells, stem-cell-like memory T cells (or stem-like memory T cells), and two types of effector memory T cells: e.g. TEM cells and TEMRA cells, Regulatory T cells (also known as suppressor T cells), Natural Killer T cells, Mucosal associated invariant T cells, and gamma-delta T cells. Cytotoxic T cells (CTL or killer T cells) are a subset of T-lymphocytes capable of inducing the death of infected somatic or tumour cells. A subject's own T cells may be genetically modified to target specific antigens through the introduction of a heterologous TCR or CAR. Preferably, the modified immunoresponsive cell is a T cell optionally a CD4+ T cell or a CD8+ T cell. Accordingly the modified immunoresponsive cells may be T-cells, optionally CD4+ T cells or CD8+ T cells, or the modified immunoresponsive cells may be a population of modified T-cells, optionally CD4+ T cells; or CD8+ T cells, or a mixed population of CD4+ T cells and CD8+ T cells.

Heterologous TCR/CAR

According to the present invention the modified immunoresponsive cells can express a heterologous T cell receptor (TCR) or heterologous chimeric antigen receptor (CAR) (e.g., the cell is transduced with or engineered to comprise a nucleic acid sequence encoding a heterologous TCR or CAR, for example by gene knock in). Upon binding to the antigen, the modified immunoresponsive cells can exhibit T cell effector functions and/or cytolytic effects towards cells bearing the antigen and/or undergo proliferation and/or cell division. In certain embodiments, the modified immunoresponsive cells comprising the heterologous TCR exhibits comparable or better therapeutic potency compared to cells comprising a chimeric antigen receptor (CAR) targeting the same cancer and/or tumour antigen and/or peptide (antigenic peptide). Activated modified immunoresponsive cells comprising the heterologous TCR or CAR can secrete anti-tumour cytokines which can include, but are not limited to, TNFalpha, IFNy and IL2.

According to the invention the modified immunoresponsive cells may comprise a nucleic acid, construct or vector, or heterologous nucleic acid, construct or vector, encoding a heterologous T cell receptor (TCR) or heterologous chimeric antigen receptor (CAR). Optionally the TCR may be an affinity enhanced TCR, for example a specific peptide enhanced affinity receptor (SPEAR) TCR.

The term "heterologous" or "exogenous" refers to a polypeptide or nucleic acid that is foreign to a particular biological system, such as a cell or host cell, and is not naturally present in that system and which may be introduced to the system by artificial or recombinant means. Accordingly, the expression of a TCR or CAR which is heterologous, may thereby alter the immunogenic specificity of the immunogenic cells, for example T cells, so that they recognise or display improved recognition for one or more tumour or cancer antigens and/or peptides that are present on the surface of the cancer cells of an individual with cancer. The modification of immunogenic cells or T cells and their subsequent expansion may be performed in vitro and/or ex vivo.

Cancer/Tumour Antigen or Peptide Antigen

According to the present invention the cancer and/or tumour antigen or peptide antigen thereof may be a cancer-testis antigen, such as a MAGE, melanoma associated antigen or member of the MAGEA gene family, for example any one of MAGE A1, A2, A3, A4, A5, A6, A7, A8, A9, A10, A11, or A12, or peptide antigen thereof. Preferably the tumour antigen is MAGE-A4, SEQ ID No:1, or peptide antigen thereof. Preferably the cancer and/or tumour antigen peptide comprises or has the amino acid sequence GVYDGREHTV, SEQ ID NO: 2.

Co-Stimulatory Ligand

According to the present invention, the modified immunoresponsive cells, may further comprise an exogenous or a recombinant (e.g., the cell is transduced with or engineered to comprise a nucleic acid sequence encoding a co-stimulatory ligand, for example by gene knock in) at least one co-stimulatory ligand, optionally one, two, three or four. The modified immunoresponsive cells, may co-express the heterologous TCR or CAR and the at least one exogenous or heterologous co-stimulatory ligand. The interaction between the heterologous TCR or CAR and at the least one exogenous co-stimulatory ligand may provide a non-antigen-specific signal and/or activation of the cell. Co-stimulatory ligands include, but are not limited to, members of the tumour necrosis factor (TNF) superfamily, and immunoglobulin (lg) superfamily ligands. TNF is a cytokine involved in systemic inflammation and stimulates the acute phase reaction. TNF superfamily members include, but are not limited to, nerve growth factor (NGF), CD40L (CD40L)/CDI54, CD137L/4-1BBL, TNF-alpha, CD134L/OX40L/CD252, CD27L/CD70, Fas ligand (FasL), CD30L/CD153, tumour necrosis factor beta (TNFP)/lymphotoxin-alpha (LTa),lymphotoxin-beta (TTb), CD257/B cell-activating factor (BAFF)/Blys/THANK/Tall-I, glucocorticoid-induced TNF Receptor ligand (GITRL), and TNF-related apoptosis-inducing ligand (TRAIL), LIGHT (TNFSF14). The immunoglobulin (lg) superfamily is a large group of cell surface and soluble proteins that are involved in the recognition, binding, or adhesion processes of cells. These proteins share structural features with immunoglobulins-they possess an immunoglobulin domain (fold). Immunoglobulin superfamily ligands include, but are not limited to, CD80 and CD86, both ligands for CD28. In certain embodiments, the at least one co-stimulatory ligand is selected from the group consisting of 4-1BBL, CD275, CD80, CD86, CD70, OX40L, CD48, TNFRSF14, and combinations thereof. The at least one exogenous or recombinant co-stimulatory ligand can be 4-1BBL or CD80, preferably, the at least one exogenous or recombinant co-stimulatory ligand is 4-1BBL. The modified immunoresponsive cells may comprise two exogenous or recombinant co-stimulatory ligands, preferably the two exogenous or recombinant co-stimulatory ligands are 4-1BBL and CD80.

The modified immunoresponsive cells may comprise an exogenous or a recombinant (e.g., the cell is transduced with or engineered to express, for example by gene knock in) at least one construct which overcomes the immunosuppressive tumour microenvironment. Such constructs can be, but are not limited to, cyclic AMP phosphodiesterases and dominant-negative transforming growth factor beta (TGF-beta) receptor II. The modified immunoresponsive cell, modified T cell or a population of modified T cells may be engineered to release cytokines which have a positive effect on the cytolytic activity of said cells. Such cytokines include, but are not limited to interleukin-7, interleukin-15 and interleukin-21.

Specific Binding TCR/CAR

According to the invention the modified immunoresponsive cells, for example modified T cells, may be modified to express a heterologous TCR or CAR, which binds or specifically binds to tumour cells and/or tissue and/or cancer cells and/or tissue of a subject, patient or cancer patient suffering from a disease condition or cancerous condition optionally which expresses or presents a to a cancer and/or tumour antigen or peptide antigen thereof as herein described. The subject, patient or cancer patient may be subsequently treated with the modified immunoresponsive cell(s) or modified T cell(s) or population thereof according to the invention. Suitable cancer patients for treatment according to the invention with the modified immunoresponsive cells or modified T cells may be identified by a method comprising; obtaining sample of tumour and/or cancer cells from an individual or subject with tumour and/or cancer and; identifying the cancer cells as binding to the TCR or CAR expressed by the modified immunoresponsive cells.

According to the invention the heterologous TCR or CAR binds or specifically binds to a cancer and/or tumour antigen or peptide antigen thereof. According to the invention the heterologous TCR or CAR binds or specifically binds to a cancer and/or tumour antigen or peptide antigen thereof associated with a cancerous condition and/or presented by tumour or cancer cell or tissue.

According to the invention the invention the cancerous condition may be head and neck or lung cancer and/or tumour.

Specificity describes the strength of binding between the heterologous TCR or CAR and a specific target cancer and/or tumour antigen or peptide antigen thereof and may be described by a dissociation constant, Kd, the ratio between bound and unbound states for the receptor-ligand system. Additionally, the fewer different cancer and/or tumour antigens or peptide antigen thereof the heterologous TCR or CAR can bind, the greater its binding specificity.

According to the invention the heterologous TCR or CAR may bind to less than 10, 9, 8, 7, 6, 5, 4, 3, 2 different cancer and/or tumour antigens or peptide antigen thereof.

According to the invention the heterologous TCR or CAR may bind, for example to MAGE A4, or an antigenic peptide thereof, for example Human MAGE A4 or MAGE A4 of SEQ ID NO: 1 or an antigenic peptide thereof or to an antigenic peptide comprising or consisting of SEQ ID NO: 2, GVYDGREHTV, with a dissociation constant of between, 0.01UM and 100 μM, between 0.01UM and 50 μM, between 0.01UM and 20 μM, between 0.05UM and 20 μM or of 0.01, 0.02, 0.03, 0.04, 0.05, 0.06, 0.07, 0.08, 0.09, 0.1 μM, 0.15 μM, 0.2 μM, 0.25M, 0.3 μM, 0.35 μM, 0.4 μM, 0.45 μM, 0.5 μM, 0.55 μM, 0.6 μM, 0.65 μM, 0.7 μM, 0.75 μM, 0.8 μM, 0.85 μM, 0.9 μM, 0.95 μM, 1.0 μM, 1.5 μM, 2.0 μM, 2.5 μM, 3.0 μM, 3.5 μM, 4.0 μM, 4.5 μM, 5.0 μM, 5.5 μM, 6.0 μM, 6.5 μM, 7.0 μM, 7.5 μM, 8.0 μM, 8.5 μM, 9.0 μM, 9.5 μM, 10.0 μM; or between 10 μM and 1000 μM, between 10 μM and 500 μM, between 50 μM and 500 μM or of 10, 20 30, 40, 50 60, 70, 80, 90, 100 μM, 150 μM, 200 μM, 250 μM, 300 μM, 350 μM, 400 μM, 450 μM, 500 μM; optionally measured with surface plasmon resonance, optionally at 25° C., optionally between a pH of 6.5 and 6.9 or 7.0 and 7.5. The dissociation constant, $K_D$ or $K_{off}/K_{on}$ may be determined by experimentally measuring the dissociation rate constant, $K_{off}$, and the association rate constant, $K_{on}$. A TCR dissociation constant may be measured using a soluble form of the TCR, wherein the TCR comprises a TCR alpha chain variable domain and a TCR beta chain variable domain. Accordingly, a heterologous TCR or CAR for use in accordance with the invention is capable of binding efficiently and/or with high affinity to HLA displaying GVYDGREHTV, SEQ ID NO: 2 optionally in complex with a peptide presenting molecule for example an HLA, for example with HLA-A*02 or HLA-A*0201, alternatively without presentation in complex with a peptide presenting molecule, for example with a dissociation constant of between 0.01 μM and 100 μM such as 50 μM, 100 μM, 200 μM, 500 μM, preferably between 0.05 μM to 20.0 M.

According to the present invention the modified immuneresponsive cells, for example modified T-cells, may comprise a heterologous TCR or CAR which may bind, specifically bind and/or bind with high affinity to a cancer and/or tumour antigen or peptide antigen thereof optionally associated with a cancerous condition and/or presented by tumour of cancer cell or tissue; optionally wherein the cancer and/or tumour antigen or peptide antigen thereof is recognised by the heterologous TCR or CAR, optionally in complex with a peptide presenting molecule for example an HLA, for example with HLA-A*02 or HLA-A*0201, alternatively without presentation in complex with a peptide presenting molecule for example or HLA (i.e. MAGE-A4 or a peptide antigen thereof or a peptide antigen of MAGE A4 comprising GVYDGREHTV, SEQ ID NO: 2 may be presented independently of a peptide presenting molecule). For example wherein the cancer and/or tumour antigen or peptide antigen thereof is MAGE A4, or an antigenic peptide thereof, for example Human MAGE A4 or MAGE A4 of SEQ ID NO: 1 or an antigenic peptide thereof or an antigenic peptide comprising or consisting of SEQ ID NO: 2, GVYDGREHTV.

According to the present invention the heterologous T cell receptor (TCR) or CAR, and modified immunoresponsive cells comprising the heterologous T cell receptor (TCR) or CAR may have the property of binding to an endogenously expressed tumour cell surface a cancer and/or tumour antigen or peptide antigen thereof optionally wherein the binding is independent of presentation of the cell surface antigen as a complex with an peptide-presenting or antigen-presenting molecule, for example major histocompatibility complex (MHC) or human leukocyte antigen (HLA) or major histocompatibility complex class related protein (MR) 1. For example wherein the cancer and/or tumour antigen or peptide antigen thereof is MAGE A4, or an antigenic peptide thereof, for example Human MAGE A4 or MAGE A4 of SEQ ID NO: 1 or an antigenic peptide thereof or an antigenic peptide comprising or consisting of SEQ ID NO: 2, GVYDGREHTV.

According to the present invention the TCR or CAR binding may be specific for one cancer and/or tumour antigen, for example Human MAGE A4 or MAGE A4 of SEQ ID NO: 1 or an antigenic peptide thereof or an antigenic peptide comprising or consisting of SEQ ID NO: 2, GVYDGREHTV, optionally in comparison to a closely related cancer and/or tumour antigen or peptide antigen sequence. The closely related cancer and/or tumour antigen or peptide antigen sequence may be of similar or identical length and/or may have a similar number or identical number of amino acid residues. The closely related peptide antigen sequence may share between 50 or 60 or 70 or 80 to 90% identity, preferably between 80 to 90% identity and/or may differ by 1, 2, 3 or 4 amino acid residues. The closely related peptide sequence may be derived from the polypeptide sequence comprising the sequence or having the sequence GVYDGREHTV, SEQ ID NO: 2.

The binding affinity may be determined by equilibrium methods (e.g. enzyme-linked immunosorbent assay (ELISA) or radioimmunoassay (RIA)), or kinetics (e.g. BIACORE™ analysis). Avidity is the sum total of the strength of binding of two molecules to one another at multiple sites, e.g. taking into account the valency of the interaction. According to the invention the immunoresponsive cells may demonstrate improved affinity and/or avidity to a cancer and/or tumour antigen or peptide antigen thereof, or a cancer and/or tumour antigen or peptide antigen thereof presented by tumour of cancer cell or tissue and recognised by the heterologous TCR or CAR in comparison in comparison to immunoresponsive cells lacking the heterologous TCR or CAR or having an alternative heterologous TCR or CAR.

Selective Binding TCR/CAR

According to the invention, the heterologous TCR or CAR may selectively bind to a cancer and/or tumour antigen or peptide antigen thereof, optionally associated with a cancerous condition and/or presented by tumour of cancer cell or tissue; optionally wherein the cancer and/or tumour antigen or peptide antigen thereof is recognised by the heterologous TCR or CAR, optionally in complex with a peptide presenting molecule for example major histocompatibility complex (MHC) or an HLA, optionally class I or II, for example with HLA-A2, or selected from HLA-A*02, HLA-A*02:01, HLA-A*02:02, HLA-A*02:03, HLA-A*02:04, HLA-A*02:06, HLA-A*02:642 or HLA-A*02:07, preferably HLA-A*02:01 or HLA-A*02; alternatively without presentation in complex with a peptide presenting molecule or HLA, preferably expressed by a tumour cell or a cancer cell or tissue. Preferably wherein the cancerous condition is head and neck or lung cancer and/or tumour.

Selective binding denotes that the heterologous TCR or CAR binds with greater affinity to one cancer and/or tumour antigen or peptide antigen thereof in comparison to another. Selective binding is denoted by the equilibrium constant for the displacement by one ligand antigen of another ligand antigen in a complex with the heterologous TCR or CAR.

According to the invention the invention the cancerous condition may be head and neck or lung cancer and/or tumour.

Specific/Selective Binding TCR/CAR

According to the present invention the heterologous TCR or CAR binding is selective and/or specific for a cancer and/or tumour antigen or peptide antigen thereof which may be MAGE-A4, or peptide antigen thereof. Preferably the tumour antigen is MAGE-A4 or peptide antigen thereof. Preferably the cancer and/or tumour antigen peptide comprises or has the amino acid sequence GVYDGREHTV, SEQ ID NO: 2. According to the present invention the heterologous TCR or CAR may bind and/or bind specifically and/or bind selectively a peptide presenting molecule for example an HLA presenting or displaying a cancer and/or tumour antigen or peptide antigen thereof, i.e. a peptide fragment of a cancer and/or tumour antigen (pHLA), wherein the HLA corresponds to MHC class I (A, B, and C) which all are the HLA Class1 or specific alleles thereof or the HLA corresponds to MHC class II (DP, DM, DO, DQ, and DR) or specific alleles thereof, preferably the HLA is class 1, preferably the allele is HLA-A2 or HLA-A*02 or an HLA-A2+ or HLA-A*02 positive HLA, preferably HLA-*0201. Alternatively, the heterologous TCR or CAR may bind and/or bind specifically and/or bind selectively a cancer and/or tumour antigen or peptide antigen thereof, which is not presented or displayed by HLA.

Preferably, the heterologous TCR or CAR is not naturally expressed by the immunoresponsive cells (i.e. the TCR or CAR is exogenous or heterologous). A heterologous TCR may include αβTCR heterodimers. A heterologous TCR or CAR may be a recombinant or synthetic or artificial TCR or CAR i.e. a CAR or TCR that does not exist in nature. For example, a heterologous TCR may be engineered to increase its affinity or avidity for a specific cancer and/or tumour antigen or peptide antigen thereof (i.e. an affinity enhanced TCR or specific peptide enhanced affinity receptor (SPEAR) TCR). The affinity enhanced TCR or (SPEAR) TCR may comprise one or more mutations relative to a naturally occurring TCR, for example, one or more mutations in the hypervariable complementarity determining regions (CDRs) of the variable regions of the TCR $\alpha$ and $\beta$ chains. These mutations may increase the affinity of the TCR for a peptide fragment of a cancer and/or tumour antigen or peptide antigen thereof or MHCs that display a peptide fragment of a cancer and/or tumour antigen optionally when expressed by tumour and/or cancer cells and/or tissue. Suitable methods of generating affinity enhanced or matured TCRs include screening libraries of TCR mutants using phage or yeast display and are well known in the art (see for example Robbins et al J Immunol (2008) 180 (9): 6116; San Miguel et al (2015) Cancer Cell 28 (3) 281-283; Schmitt et al (2013) Blood 122 348-256; Jiang et al (2015) Cancer Discovery 5 901). Preferred affinity enhanced TCRs may bind to tumour or cancer cells expressing the cancer and/or tumour antigen of the MAGE family, for example MAGE A4 or peptide antigen thereof for example peptides thereof comprising or consisting of the sequence GVYDGREHTV, SEQ ID NO: 2.

According to the invention the heterologous TCR may be a MAGE A4 TCR which may comprise the a chain reference amino acid sequence of SEQ ID NO: 5 or a variant thereof and the B chain reference amino acid sequence of SEQ NO: 7 or a variant thereof. A variant may have an amino acid sequence having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity to the reference amino acid sequence (for example, with respect to either a chain reference sequence and/or β chain reference sequence). The TCR may be encoded by the a chain reference nucleotide sequence of SEQ ID NO: 6 or a variant thereof and the B chain reference nucleotide sequence of SEQ NO: 8 or a variant thereof. A variant may have a nucleotide sequence having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity to the reference nucleotide sequence (for example, with respect to either a chain reference sequence and/or @ chain reference sequence).

According to the present invention the TCR may comprise a TCR alpha chain variable domain and a TCR beta chain variable domain, wherein:

(i) the alpha chain variable domain comprises CDRs having the sequences

VSPFSN (αCDR1), SEQ ID NO:11 or amino acids 48-53 of SEQ ID NO:5,

LTFSEN (αCDR2), SEQ ID NO:12 or amino acids 71-76 of SEQ ID NO:5, and

CVVSGGTDSWGKLQF (αCDR3), SEQ ID NO:13 or amino acids 111-125 of SEQ ID NO:5, and/or (ii) the beta chain variable domain comprises CDRs having the sequences KGHDR (βCDR1), SEQ ID NO:14 or amino acids 46-50 of SEQ ID NO:7, SFDVKD (βCDR2), SEQ ID NO: 15 or amino acids 68-73 of SEQ ID NO:7, and CATSGQGAYEEQFF (βCDR3), SEQ ID NO:16 or amino acids 110-123 of SEQ ID NO:7 or sequence having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity thereto, optionally 100% sequence identity thereto, respectively.

Accordingly, the TCR may comprise a TCR in which the alpha chain variable domain comprises an amino acid sequence that has at least 70%, 75%, 80%, 85%, 90%, 95%, 96%, 97%, 98% or 99% or 100% identity to SEQ ID NO:9 or the sequence of amino acid residues 1-136 of SEQ ID NO:6, and/or the beta chain variable domain comprising an amino acid sequence that has at least 70%, 75%, 80%, 85%, 90%, 95%, 96%, 97%, 98% or 99% or 100% identity to SEQ ID NO:10 or the sequence of amino acid residues 1-133 of SEQ ID NO: 7.

The terms "progenitor TCR", is used herein to refer to a TCR comprising the MAGE A4 TCR α chain and MAGE A4 TCR β chain of SEQ ID NOs: 5 and 7 respectively. It is desirable to provide TCRs that are mutated or modified relative to the progenitor TCR that have an equal, equivalent or higher affinity and/or an equal, equivalent or slower off-rate for the peptide-HLA complex than the progenitor TCR. According to the invention the heterologous TCR may have more than one mutation present in the alpha chain variable domain and/or the beta chain variable domain relative to the progenitor TCR and may be denoted, "engineered TCR" or "mutant TCR". These mutation(s) may improve the binding affinity and/or specificity and/or selectivity and/or avidity for MAGE A4 or peptide antigen thereof. In certain embodiments, there are 1, 2, 3, 4, 5, 6, 7 or 8 mutations in alpha chain variable domain, for example 4 or 8 mutations, and/or 1, 2, 3, 4 or 5 mutations in the beta chain variable domain, for example 5 mutations. In some embodiments, the a chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues of SEQ ID NO: 9. In some embodiments, the B chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues of SEQ ID NO: 10.

According to the invention the heterologous TCR may comprise a TCR in which, the alpha chain variable domain comprises SEQ ID NO: 9 or the amino acid sequence of amino acid residues 1-136 of SEQ ID NO:5, or an amino acid sequence in which amino acid residues 1-47, 54-70, 77-110 and 126-136 thereof have at least 70%, 75%, 80%, 85%, 90%, 95%, 96%, 97%, 98% or 99% identity to the sequence of amino acid residues 1-47, 54-70, 77-110 and 126-136 respectively of SEQ ID NO:9 and/or in which amino acid residues 48-53, 71-76 and 111-125, CDR 1, CDR 2, CDR 3 respectively, have at least 70%, 75%, 80%, 85%, 90%, 95%, 96%, 97%, 98% or 99% identity to the sequence of amino acid residues 48-53, 71-76 and 111-125, CDR 1, CDR 2, CDR 3, respectively of SEQ ID NO:9.

According to the invention, the TCR may comprise a TCR in which, in the alpha chain variable domain, the sequence of:

(i) amino acid residues 1-47 thereof may have (a) at least 70%, 75%, 80%, 85%, 90% or 95% identity to the sequence of amino acid residues 1-47 of SEQ ID NO:9 or (b) may have one, two or three amino acid residues inserted or deleted relative to residues 1-47 of SEQ ID NO: 9, (ii) amino acid residues 48-53 is VSPFSN, CDR 1, SEQ ID NO:11 or amino acids 48-53 of SEQ ID NO:9, (iii) amino acid residues 54-70 thereof may have (a) at least 70%, 75%, 80%, 85%, 90% or 95% identity to the sequence of amino acid residues 54-70 of SEQ ID NO: 9 or (b) may have one, two or three amino acid residues inserted or deleted relative to the sequence of amino acid residues 54-70 of SEQ ID NO: 9, (iv) amino acid residues 71-76 may be LTFSEN, CDR 2, SEQ ID NO:12 or amino acids 71-76 of SEQ ID NO:9, (v) amino acid residues 77-110 thereof may have at least 70%, 75%, 80%, 85%, 90% or 95% identity to the sequence of amino acid residues 77-110 of SEQ ID NO:9 or may have one, two or three insertions, deletions or substitutions relative to the sequence of amino acid residues 77-110 of SEQ ID NO:9, (vi) amino acids 111-125 may be CVVSGGTDSWGKLQF, CDR 3, SEQ ID NO:13 or amino acids 111-125 of SEQ ID NO:9, (vii) amino acid residues 126-136 thereof may have at least 70%, 75%, 80%, 85%, 90% or 95% identity to the sequence of amino acid residues 126-136 of SEQ ID NO: 9 or may have one, two or three insertions, deletions or substitutions relative to the sequence of amino acid residues 126-136 of SEQ ID NO:9.

According to the invention, the TCR may comprise a TCR in which, in the beta chain variable domain comprises the amino acid sequence of SEQ ID NO:10, or an amino acid sequence in which amino acid residues 1-45, 51-67, 74-109, 124-133 thereof have at least 70%, 75%, 80%, 85%, 90% or 95% identity to the sequence of amino acid residues 1-45, 51-67, 74-109, 124-133 respectively of SEQ ID NO:10 and in which amino acid residues 46-50, 68-73 and 110-123 have at least 70%, 75%, 80%, 85%, 90% or 95% identity to the sequence of amino acid residues 46-50, 68-73 and 110-123, CDR 1, CDR 2, CDR 3, respectively of SEQ ID NO: 10.

According to the invention, the TCR may comprise a TCR in which, in the beta chain variable domain, the sequence of:

(i) amino acid residues 1-45 thereof may have (a) at least 70%, 75%, 80%, 85%, 90% or 95% identity to the sequence of amino acid residues 1-45 of SEQ ID NO:10 or (b) may have one, two or three amino acid residues inserted or deleted relative to residues 1-45 of SEQ ID NO: 10, (ii) amino acid residues 46-50 is KGHDR, CDR 1, SEQ ID NO:14 or amino acids 46-50 of SEQ ID NO:10, (iii) amino acid residues 51-67 thereof may have (a) at least 70%, 75%, 80%, 85%, 90% or 95% identity to the sequence of amino acid residues 51-67 of SEQ ID NO:10 or (b) may have one, two or three amino acid residues inserted or deleted relative to the sequence of amino acid residues 51-67 of SEQ ID NO:10, (iv) amino acid residues 68-73 may be SFDVKD, CDR 2, SEQ ID NO:15 or amino acids 68-73 of SEQ ID NO:10, (v) amino acid residues 74-109 thereof may have at least 70%, 75%, 80%, 85%, 90% or 95% identity to the sequence of amino acid residues 74-109 of SEQ ID NO:10 or may have one, two or three insertions, deletions or substitutions relative to the sequence of amino acid residues 74-109 of SEQ ID NO:10;

(vi) amino acids 110-123 may be CATSGQGAYEEQFF, CDR 3, SEQ ID NO:16 or amino acids 110-123 of SEQ ID NO:10, (vii) amino acid residues 124-133 thereof may have at least 70%, 75%, 80%, 85%, 90% or 95% identity to the sequence of amino acid residues 124-133 of SEQ ID NO:10 or may have one, two or three insertions, deletions or substitutions relative to the sequence of amino acid residues 124-133 of SEQ ID NO:10.

According to the invention, the TCR may comprise a TCR which comprises an alpha chain variable domain of SEQ ID NO: 9 and/or a beta chain variable domain of SEQ ID NO: 10. According to the invention, the TCR may comprise a TCR which comprises an alpha chain of SEQ ID NO: 5 and/or a beta chain of SEQ ID NO: 7.

Amino acid and nucleotide sequence identity is generally defined with reference to the algorithm GAP (GCG Wisconsin Package™, Accelrys, San Diego CA). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST, psiBLAST or TBLASTN (which use the method of Altschul et al. (1990) *J. Mol. Biol.* 215:405-410), FASTA (which uses the method of Pearson and Lipman (1988) *PNAS USA* 85:2444-2448), or the Smith-Waterman algorithm (Smith and Waterman (1981) *J. Mol Biol.* 147: 195-197), generally employing default parameters.

Particular amino acid sequence variants may differ from a reference sequence by insertion, addition, substitution or deletion of 1 amino acid, 2, 3, 4, 5-10, 10-20 or 20-30 amino acids. In some embodiments, a variant sequence may comprise the reference sequence with 1, 2, 3, 4, 5, 6, 7, 8, 9, 10 or more residues inserted, deleted or substituted. For example, up to 15, up to 20, up to 30 or up to 40 residues may be inserted, deleted or substituted. In some preferred embodiments, a variant may differ from a reference sequence by 1, 2, 3, 4, 5, 6, 7, 8, 9, 10 or more conservative substitutions. Conservative substitutions involve the replacement of an amino acid with a different amino acid having similar properties. For example, an aliphatic residue may be replaced by another aliphatic residue, a non-polar residue may be replaced by another non-polar residue, an acidic residue may be replaced by another acidic residue, a basic residue may be replaced by another basic residue, a polar residue may be replaced by another polar residue or an aromatic residue may be replaced by another aromatic residue. Conservative substitutions may, for example, be between amino acids within the following groups:

alanine and glycine;
glutamic acid, aspartic acid, glutamine, and asparagine
arginine and lysine;
asparagine, glutamine, glutamic acid and aspartic acid
isoleucine, leucine and valine;
phenylalanine, tyrosine and tryptophan
serine, threonine, and cysteine.

The CD8α Co-Receptor

According to the present invention, the modified immunoresponsive cells expressing or presenting a heterologous TCR or CAR may further express or present a heterologous co-receptor (e.g., the cell is transduced with or engineered to comprise a nucleic acid sequence encoding a co-receptor, for example by gene knock in). The heterologous co-receptor may be a CD8 co-receptor. The CD8 co-receptor may comprise a dimer or pair of CD8 chains which comprises a CD8-α and CD8-β chain or a CD8-α and CD8-α chain. Preferably, the CD8 co-receptor is a CD8aa co-receptor comprising a CD8-α and CD8-α chain. A CD8α co-receptor may comprise the amino acid sequence of at least 80% identity to SEQ ID NO: 3, SEQ ID NO: 3 or a variant thereof. The CD8α co-receptor may be a homodimer.

The CD8 co-receptor binds to class 1 MHCs and potentiates TCR signalling. According to the invention the CD8 co-receptor may comprise the reference amino acid sequence of SEQ ID NO: 3 or may be a variant thereof. A variant may have an amino acid sequence having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity to the reference amino acid sequence SEQ ID NO: 3. The CD8 co-receptor may be encoded by the reference nucleotide sequence of SEQ ID NO: 4 or may be a variant thereof. A variant may have a nucleotide sequence having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity to the reference nucleotide sequence SEQ ID NO: 4.

According to the invention the heterologous CD8 co-receptor may comprise a CD8 co-receptor in which, in the Ig like V-type domain comprises CDRs having the sequence;

(i) VLLSNPTSG, CDR1, SEQ ID NO: 17, or amino acids 45-53 of SEQ ID NO: 3, (ii) YLSQNKPK, CDR2, SEQ ID NO: 18 or amino acids 72-79 of SEQ ID NO: 3, (iii) LSNSIM, CDR3, SEQ ID NO: 19 or amino acids 80-117 of SEQ ID NO: 3, or sequences having at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% sequence identity thereto.

According to the invention the heterologous CD8 co-receptor may comprise a CD8 co-receptor which comprises or in which, in the Ig like V-type domain comprises, residues 22-135 of the amino acid sequence of SEQ ID No:3, or an amino acid sequence in which amino acid residues 22-44, 54-71, 80-117, 124-135 thereof have at least 70%, 75%, 80%, 85%, 90% or 95% identity to the sequence of amino acid residues 22-44, 54-71, 80-117, 124-135, CDR 1, CDR 2, CDR 3, respectively of SEQ ID No:3 and in which amino acid residues 45-53, 72-79 and 118-123 have at least 70%, 75%, 80%, 85%, 90% or 95% identity to the sequence of amino acid residues 45-53, 72-79 and 118-123 respectively of SEQ ID No:3.

According to the invention the CD8 co-receptor may comprise a CD8 co-receptor in which, or in which in the Ig like V-type domain, the sequence of:

(i) amino acid residues 22-44 thereof may have (a) at least 70%, 75%, 80%, 85%, 90% or 95% identity to the sequence of amino acid residues 22-44 of SEQ ID NO:3 or (b) may have one, two or three amino acid residues inserted or deleted relative to residues 22-44 of SEQ ID NO: 3, (ii) amino acid residues 45-53 is VLLSNPTSG, SEQ ID NO:17, CDR1, or amino acids 45-53 of SEQ ID NO:3, (iii) amino acid residues 54-71 thereof may have (a) at least 70%, 75%, 80%, 85%, 90% or 95% identity to the sequence of amino acid residues 54-71 of SEQ ID NO:3 or (b) may have one, two or three amino acid residues inserted or deleted relative to the sequence of amino acid residues 54-71 of SEQ ID NO:3, (iv) amino acid residues 72-79 may be YLSQNKPK, CDR2, SEQ ID NO:18 or amino acids 72-79 of SEQ ID NO:3, (v) amino acid residues 80-117 thereof may have at least 70%, 75%, 80%, 85%, 90% or 95% identity to the sequence of amino acid residues 80-117 of SEQ ID NO:3 or may have one, two or three insertions, deletions or substitutions relative to the sequence of amino acid residues 80-117 of SEQ ID NO:3;

(vi) amino acids 118-123 may be LSNSIM, CDR3, SEQ ID NO:19 or amino acids 80-117 of SEQ ID NO:3, (vii) amino acid residues 124-135 thereof may have at least 70%, 75%, 80%, 85%, 90% or 95% identity to the sequence of amino acid residues 124-135 of SEQ ID NO:3 or may have one, two or three insertions, deletions or substitutions relative to the sequence of amino acid residues 124-135 of SEQ ID NO:3.

The modified immunoresponsive cells that express heterologous CD8 co-receptor may demonstrate improved affinity and/or avidity and/or improved T-cell activation, as determinable by the assays disclosed herein, towards or on stimulation by antigenic peptide, tumour or cancer antigen optionally when presented on HLA relative to modified immunoresponsive cells that do not express heterologous CD8 co-receptor. The heterologous CD8 of modified immunoresponsive cells may interact or bind specifically to an MHC, the MHC may be class I or class II, preferably class I major histocompatibility complex (MHC), HLA-I molecule or with the MHC class I HLA-A/B2M dimer, preferably the CD8-α interacts with the $a_3$ portion of the Class I MHC (between residues 223 and 229), preferably via the IgV-like domain of CD8. Accordingly the heterologous CD8 improves TCR binding of the immunoresponsive cells to the HLA and/or antigenic peptide bound or presented by HLA pMHCI or pHLA, optionally on the surface of antigen presenting cell, dendritic cell and/or tumour or cancer cell, tumour or cancer tissue compared to immunoresponsive cells lacking the heterologous CD8. Accordingly the heterologous CD8 can improve or increase the off-rate ($K_{off}$) of the cell (TCR)/peptide-major histocompatibility complex class I (pMHCI) interaction of the immunoresponsive cells, and hence its half-life, optionally on the surface of antigen presenting cell, dendritic cell and/or tumour or cancer cell, or tumour or cancer tissue compared to the cells lacking the heterologous CD8, and thereby may also provide improved ligation affinity and/or avidity. The heterologous CD8 can improve organizing the TCR on the immunoresponsive cell surface to enable cooperativity in pHLA binding and may provide improved therapeutic avidity. Accordingly, the heterologous CD8 co-receptor modified immunoresponsive cells may bind or interact with LCK (lymphocyte-specific protein tyrosine kinase) in a zinc-dependent manner leading to activation of transcription factors like NFAT, NF-κB, and AP-1.

According to the invention the modified immunoresponsive cells may have an improved or increased expression of CD40L, cytokine production, cytotoxic activity, induction of dendritic cell maturation or induction of dendritic cell cytokine production, optionally in response to cancer and/or tumour antigen or peptide antigen thereof optionally as presented by tumour of cancer cell or tissue, in comparison to immunoresponsive cells lacking the heterologous CD8 co-receptor.

Therapy

Head and Neck Cancer

According to the present invention the cancer may be head and neck cancer, carcinoma or tumour which may be primary, secondary, recurrent, metastatic or advanced head and neck cancer, carcinoma or tumour. Preferably the head and neck cancer may be selected from any one of head and neck cancer, head and neck squamous cell carcinoma (HNSCC), cancer of the oral cavity, cancer of the oropharynx, cancer of the hypopharynx, cancer of the throat, cancer of the larynx, cancer of the the tonsil, cancer of the tongue, cancer of the soft palate, cancer of the pharynx. Accordingly, the cancer may be oral cancer or carcinoma or cancer or carcinoma of the mouth including squamous cell cancer of the inner lip, lip, tongue, floor of mouth, gums, hard palate.

Accordingly the cancer may be nasal cancer or carcinoma or squamous cell carcinoma, including paranasal sinus and nasal cavity cancer affects the nasal cavity and the paranasal sinuses or nasopharynx cancer including cancer which arises in the nasopharynx, the nasal cavities and the Eustachian tubes and upper part of the throat, the cancer may also be lymphoepithelioma.

Accordingly the cancer may be throat cancer for example oropharyngeal cancer, oropharyngeal squamous cell carcinoma, HPV-positive oropharyngeal cancer or HPV-positive oropharyngeal squamous cell carcinoma, optionally wherein the squamous cell carcinoma is of the oropharynx or throat including the soft palate, the base of the tongue, and the tonsils.

Accordingly the cancer may be Hypopharyngeal cancer including cancer of the pyriform sinuses, the posterior pharyngeal wall, or the postcricoid area or metastases thereof to the lymphatic network around the larynx.

Accordingly the cancer may be laryngeal cancer, including cancer of the larynx, glottic cancer, supraglottic or subglottic cancer.

Accordingly the cancer may be, cancer of the trachea, cancer or squamous cell carcinomas of the salivary glands teratoma, adenocarcinoma, adenoid cystic carcinoma, and mucoepidermoid carcinoma or melanomas or lymphomas of the upper aerodigestive tract.

Accordingly the cancer may be metastatic head and neck cancer that has metastasised to the adrenal gland, skin, liver pleura, bone, lung, or mediastinal lymph nodes.

Accordingly the head and neck cancer, carcinoma or tumour may express a MAGE protein, peptide, antigen or peptide antigen thereof, optionally MAGE-A4 protein, peptide, antigen or peptide antigen thereof as herein described. According to the invention the cancer may be recurrent or metastatic HNSCC, optionally with disease progression on after platinum containing chemotherapy, optionally expressing MAGE-A4 protein, peptide, antigen or peptide antigen thereof as described herein (for example a peptide antigen of MAGE A4 comprising GVYDGREHTV, SEQ ID NO: 2).

Lung Cancer

According to the present invention the cancer may be lung cancer, carcinoma or tumour which may be primary, secondary, recurrent, metastatic or advanced lung cancer, carcinoma or tumour. Preferably the lung cancer, carcinoma or tumour is selected from any of; large-cell cancer or large-cell carcinoma of the lung, small cell lung cancer or small cell lung carcinoma (SCLC), SCLC of the primary and secondary bronchi, non-small cell lung cancer or non-small cell lung carcinoma (NSCLC), metastatic or advanced NSCLC, squamous NSCLC, adenosquamous NSCLC, adenocarcinoma NSCLC, large cell NSCLC, adenocarcinoma, bronchioloalveolar carcinoma, pulmonary enteric adenocarcinoma, squamous-cell carcinoma, adenosquamous carcinoma, carcinoid tumour, bronchial gland carcinomas, sarcomatoid carcinoma.

Accordingly the cancer may be metastatic lung cancer that has metastasised to the brain, bones, liver, or adrenal glands. Accordingly the lung cancer may be lung cancer that has invaded the diaphragm, mediastinum, heart, superior vena cava, inferior vena cava, pulmonary arteries, pulmonary veins, aorta, trachea, carina of the trachea, recurrent laryngeal nerve, oesophagus, spine or vertebral body.

Accordingly the lung cancer, carcinoma or tumour expresses a MAGE protein, peptide, antigen or peptide antigen thereof, optionally MAGE-A4 protein, peptide, antigen or peptide antigen thereof. According to the invention the cancer may be recurrent or metastatic the lung cancer, carcinoma or tumour, optionally with disease progression on after platinum containing chemotherapy, optionally expressing MAGE-A4 protein, peptide, antigen or peptide antigen thereof as described herein (for example a peptide antigen of MAGE A4 comprising GVYDGREHTV, SEQ ID NO: 2).

Standard of Care

The standard of care for lung cancer or tumour can be systemic platinum-based chemotherapy and may be selected from cisplatin or carboplatin chemotherapy treatment. Alternatively the standard of care for lung cancer or tumour can be selected from treatment with any one of ifosfamide, mytomycin C, vindesine, vinblastine, etoposide, gemcitabine, paclitaxel, docetaxel, vinorelbine, pemetrexed, erlotinib, gefitinib, bevacizumab.

The standard of care for head and neck cancer or tumour may be systemic platinum-based chemotherapy selected from cisplatin or carboplatin chemotherapy treatment or may be a platinum-based combination chemotherapy treatment for example selected from a combination of cisplatin or carboplatin in combination with any one of cetuximab or fluorouracil or a taxane such as paclitaxel (Taxol) or docetaxel. Alternatively the standard of care for head and neck cancer or tumour may be selected from treatment with any one of a PD-1 antibody, for example pembrolizumab or nivolumab, cetuximab or cetuximab in combination with any one of fluorouracil, methotrexate, cisplatin, carboplatin or a taxane such as paclitaxel (Taxol) or docetaxel.

Accordingly the present invention and the methods, treatment and uses of the present invention provides a reduction in MAGE-A4 expression or concentration in a subject in comparison to placebo treatment or in comparison to without treatment or compared to pre-treatment, or in comparison to treatment comprising a standard of care.

Disease Biomarkers

The present invention and the methods, treatment and uses and/or kits of the present invention provides a treatment, prevention or delay in the progression of head and neck or lung cancer and/or tumour in a subject as determined by subject disease biomarker changes in expression or concentration compared to the pre-treatment disease biomarker expression or concentration or in comparison placebo treatment or to without treatment or in comparison to treatment comprising a standard of care.

Changes in disease biomarker levels from Baseline (pre-treatment) are correlated with response to treatment and correspond to treatment efficacy and success of cancer and/or tumour treatment.

Disease biomarkers of head and neck cancer or tumour may be selected from any one or more of; CXC chemokine receptor 2 (CXCR2) expression or mRNA expression, CC chemokine receptor 4 (CCR4) expression or mRNA expression, CC chemokine receptor 7 (CCR7) expression or mRNA expression, human papilloma virus (HPV) viral protein expression or concentration, e.g. HPV16 or 18 oncoprotein expression, for example E6 or E7 oncoproteins, detected loss of heterozygosity in tumour cell derived DNA, the presence or level of hypermethylation of cytosine-phosphate-guanine (CpG)-rich promoter regions, metalloproteinase expression, e.g. MMP-1 or the gelatinases MMP-2 or MMP-9 or the stromelysins, MMP-3 and MMP-10, Interleukin IL-6 and IL-8 levels or expression, expression of MAGE-A1, 2, 3, 4, 5, 6, cytokeratin (e.g. CKs 6, 16 or 17) or actin or myosin concentration or expression levels, overexpression of eukaryotic translation factor 4E (elF4E), mutation levels in DNA repair genes e.g. of the nucleotide excision repair (NER) group.

Disease biomarkers of lung cancer or tumour may be selected from any one or more of; presence or level of anaplastic lymphoma kinase (ALK) translocations, presence or level of epidermal growth factor receptor (EGFR) mutations, presence or level of Kirsten rat sarcoma viral oncogene homolog (KRAS) mutations, human epidermal growth factor receptor-2 (HER2/neu) expression, presence or level of B-Raf proto-oncogene serine/threonine kinase (BRAF) mutations, presence or level of C-KIT proto-oncogene mutations, expression of MAGE-A1, 2, 3, 4, 5, 6, presence or level of Janus kinase 2 (JAK2) mutations, Programmed Cell Death 1 (PD-1), Programmed Cell Death-Ligand 1/2 (PD-L1, PD-L2) expression level, Fibroblast growth factor receptor (FGFR) expression level, levels of hepatocellular growth factor HGF expression. Further disease biomarkers of lung cancer may include EML4-ALK tyrosine kinase fusion, epigenetic changes such as alteration of DNA methylation, histone tail modification, or microRNA regulation causing inactivation of tumour suppression, mutations and amplification of c-MET, NKX2-1, LKB1, PIK3CA, and BRAF.

Disease biomarkers can also include circulating tumour cells (CTCs), cell-free DNA, micro RNA, cell-free RNA and cell-derived vesicles, such as exosomes which may circulate in a biological sample as described herein. CTCs are disseminated tumour cells which are circulating in the bloodstream their presence is clinically related with the cancer or progressive or metastatic disease.

According to the invention disease biomarkers may be measured in a biological sample of a subject for example as described herein.

Biological Sample

A biological sample can be any subject or patient body fluid that may contain a disease biomarker or cell or genetic material from a cancer or tumour (e.g. head and neck or lung cancer and/or tumour), for instance blood, serum, plasma, urine, tissue, cells, cell cultures, saliva, sputum, cerebrospinal fluid, lavage or fluid from lung, nasal, bronchus, bronchoalveolar, esophagogastric or gastrointestinal tract, peripheral blood samples from patients or subjects with cancer containing circulating tumour cells (CTCs), cell-free DNA, micro RNA, cell-free RNA and cell-derived vesicles, such as exosomes. CTCs are disseminated tumour cells as single cells or, less commonly, as cell clusters, derived from either primary tumours or metastases which are circulating in the bloodstream. The existence of CTCs like other disease biomarkers are clinically related with tumour and/or cancer, progressive or metastatic disease. For example, in both head and neck cancer and lung cancer, disease biomarkers or biomarkers or MAGE-A4 or antibodies thereto may be detected in a biological sample for example a body fluid for example serum or saliva/sputum as biomarkers of MAGE-A4 expressing cancer and/or tumour and/or tissue.

Therapeutic Effect

Serum Cytokine and Soluble Factor Analysis and T-Cell Infiltration of Tumour

The present invention and the methods, treatment and uses of the present invention provides an increase in serum cytokine and/or interferon level or concentration in a subject compared to the pre-treatment serum cytokine and/or interferon level or concentration or in comparison to placebo treatment or without treatment or treatment comprising a standard of care.

Accordingly the invention and the methods, treatment and uses of the present invention provides an improved or enhanced cancer and/or tumour immunogenicity, for example as measured by the ability to provoke an immune response in response to cancer and/or tumour or cancer and/or tumour antigen, for example enhanced by at least 10%, alternatively 20%, 30%, 40%, 50%, 60%, 70%, 80%, 90%, 100%, 120%, 150%, 200% or more relative to such levels before the treatment or intervention or compared to placebo, or relative to without treatment or relative to treatment comprising a standard of care, for example as judged by increased secretion of cytokines and/or interferon, increased T-cell proliferation, increased antigen responsiveness, target cell killing, T-cell activation, CD28 signalling, T-cell infiltration of tumour, ability to recognise and bind to dendritic cell presented antigen.

The efficacy of immunotherapy of cancer is conditioned by the infiltration of tumours by activated tumour-specific T-cells. The activity of these T-cells will in turn be affected by the presence in the tumour of an immunosuppressive environment (e.g. regulatory T-cells). Therefore, the direct evaluation of the "immune landscape" inside the tumour is of great value for monitoring efficacy of the T-cell immunotherapy and may be quantitated by tumour biopsies to evaluate the immune status of the tumour before and after T-cell infusion. Accordingly the invention provides an improved T-cell infiltration of tumour and/or reduction in T-cell repressive factors as determined for example by a reduction in level of T-regs, Myeloid derived suppressor cells (MDSCs), PD-L1 protein expression, serum cytokine levels selected from CCL3, IL8, IL1β, CXCL10, or sIL2Rα or levels of inhibitory receptors, selected from PD-1, CTLA-4, TIM-3, LAG-3, BTLA or TIGIT compared to pre-treatment or without treatment or in comparison to treatment comprising a standard of care. Alternatively as determined from an increase in level of interferon-γ, interleukin-6, interleukin-10, cytokine production, such as IL-2, TNF-α, IFN-γ and granzyme B or innate immune cells such as NK cells, adaptive immune cells (CD4+ and CD8+) or improved proliferation in T-cells for example as judged by Ki67 expression level, compared to pre-treatment or without treatment or in comparison to treatment comprising a standard of care as herein before described.

Tumour Size and Tumour Burden

The present invention and the methods, treatment and uses of the present invention provides an improved or enhanced level or response of reducing tumour growth or tumour growth rate or maintaining tumour size after cessation of treatment or of tumour number or tumour burden, in comparison to prior to treatment or treatment with placebo or without treatment or treatment comprising a standard of care, for example, as determined by the measurement of tumour size or tumour number, preferably improved or enhanced by at least 10%, alternatively 20%, 30%, 40%, 50%, 60%, 70%, 80%, 90%, 100%, 120%, 150%, 200% or more relative to prior to treatment, treatment with placebo, or without treatment or treatment comprising a standard of care. Preferably an improved or enhanced level or response may be a sustained improved or enhanced level or response and/or may have a duration at least the same as the treatment duration, at least 1.5, 2.0, 2.5, or 3.0 or more times the length of the treatment duration. Such improved or enhanced level or response may be judged from RECIST 1.1 measurements [E. A. Eisenhauer., et. al., EUROPEAN JOURNAL OF CANCER 45 (2009) 228-247] or by tumour biopsy or liquid biopsy (plasma from peripheral blood) to determine tumour related circulating-free DNA (cfDNA) or exosomes (source of stable mRNA). Exosomes (produced by all cells, including tumour cells and immune cells) and cfDNA (produced by dying tumour cells) may be used to monitor both the tumour burden and the immune response. The analysis of exosomes and cfDNA may allow: (a) estimation and genetic profiling of the global tumour burden (including expression of MAGE-A4 mRNA or mutational profiling) from exosomes and cfDNA, (b) Systemic assessment of the immune response (gene expression by cytotoxic and regulatory immune cells) from exosomes.

According to the foregoing, the standard of care treatment may be as herein above described for the head and neck or lung cancer or tumour respectively.

MAGE-A4 TCR+ Cell Persistence

The present invention and the methods, treatment and uses of the present invention provides improved therapeutic effect and improved treatment, prevention or delaying in the progression of head and neck cancer and/or tumour or lung cancer and/or tumour in a subject, in comparison to prior to treatment, treatment with placebo or without treatment or treatment comprising a standard of care, for example, as determined by the measurement of the persistence of infused engineered and modified immunoresponsive cells expressing or presenting a heterologous T-cell receptor (TCR) as herein described. Persistence of the infused engineered and modified immunoresponsive cells is correlated with therapeutic effect and is also a long-term safety measure. Cell persistence can be determined by qPCR or flow cytometry (FCM). For example the quantitation of MAGE-A4 or MAGE-A4+CD8 TCR+ cells by PCR of transgene from DNA extracted from frozen subject PBMC may be used as a measure, likewise the quantitation of MAGE-A4 or MAGE-A4+CD8 TCR expressing cells by FCM from frozen subject PBMC. T cell phenotype and activity may be determined by a range of assays, for example:

- Phenotype analysis for determination of T-cell lineages in cell product and in the subject blood pre and post infusion.
- Quantitation of the senescence and activation status of T-cells from subject PBMC.
- Quantitation of soluble factors reflecting in vivo function of infused T cells, for example MAGE-A4 or MAGE-A4+CD8 TCR+ T-cells.
- Ex-vivo activity of transduced cells of subjects at different time points to assess potential functionality of those cells before and/or during the timeframe of treatment.

T-Cell Function

The present invention and the methods, treatment and uses of the present invention provides an enhancement of T-cell function compared to pre-treatment, treatment with placebo or in comparison to without treatment or in comparison to treatment comprising a standard of care. Preferably the T-cell function is enhanced by at least 10%, alternatively 20%, 30%, 40%, 50%, 60%, 70%, 80%, 90%, 100%, 120%, 150%, 200% or more, for example as judged by increased secretion of γ-interferon from CD8+ T-cells, increased T-cell proliferation, increased internal signalling, increased antigen responsiveness, increased secretion of cytokines and/or interferon, increased target cell killing, increased T-cell activation, increased CD28 signalling, increased T-cell ability to infiltrate tumour, increased ability to recognise and bind to dendritic cell presented antigen.

According to the present invention and the methods and uses of the present invention, tumour immunity or evasion of immune recognition by the tumour may be attenuated resulting in improved tumour recognition and attack by the immune system and thereby treating tumour immunity for example as measured by tumour binding, tumour shrinkage and tumour clearance. Accordingly, the present invention provides treatment of tumour immunity and/or provides treatment of tumour immunity which is enhanced by at least 10%, alternatively 20%, 30%, 40%, 50%, 60%, 70%, 80%, 90%, 100%, 120%, 150%, 200% or more compared to pre-treatment, treatment by placebo or in comparison to without treatment or in comparison to treatment comprising a standard of care, for example as measured by tumour binding, tumour shrinkage or tumour clearance.

In the context of T-cell activity the term "dysfunction" refers to a state of reduced immune responsiveness to antigenic stimulation and includes T-cell exhaustion and/or anergy whereby the T-cell may recognise and bind antigen, e.g. cancer and/or tumour antigen or peptide antigen thereof, but shows reduced effectiveness in progressing immune response or combating cancer progress and/or tumour growth. Dysfunctional T-cells demonstrate impaired capacity to translate antigen recognition into down-stream T-cell effector functions, such as proliferation, cytokine and interferon production or target cell killing and/or appear refractory or unresponsive to antigen recognition as is characteristic of T-cell dysfunctional disorder. "T-cell dysfunctional disorder" may be associated with or detected as inappropriate increased T-cell signalling through PD-1; T-cells having decreased ability to proliferate and/or produce cytokines and/or cytolytic activity; T-cell anergy; tumour immunity.

"T-cell exhaustion" comprises a state of T cell dysfunction due to sustained TCR signalling as part of the response to cancer and prevents optimal response to tumours. Exhaustion can find effect through either the cell intrinsic negative regulatory (costimulatory) pathways (for example PD-1, PD-1 axis, B7-H3, B7-H4) or through the cell extrinsic negative regulatory pathways (immunoregulatory cytokines). T-cell exhaustion is characterised by poor effector function, sustained expression of inhibitory receptors and an altered activity of transcription distinct from that of functional effector or memory T-cells. T-cell anergy occurs through deficient signalling through the T-cell receptor and a resulting state of unresponsiveness to antigen stimulation often even in the context of co-stimulation, consequently such T-cells do not undergo clonal expansion and/or acquire effector functions.

Treatment and Administration

According to the invention the modified immunoresponsive cells may be administered continuously or intermittently, optionally as a single dose or as more than one dose.

Accordingly the modified immunoresponsive cells may be administered as a single dose or as more than one dose (multiple doses). The modified immunoresponsive cells may be administered at a dose of between about 500 million to any one of about 1 billion cells, about 2 billion cells, about 3 billion cells, about 4 billion cells, about 5 billion cells, about 6 billion cells, about 7 billion cells, about 8 billion cells, about 9 billion cells, about 10 billion cells, about 11 billion cells, about 12 billion cells, about 13 billion cells, about 14 billion cells, about 15 billion cells, about 16 billion cells, about 17 billion cells, about 18 billion cells, about 19 billion cells, about 20 billion cells, or about 21 billion cells. The modified immunoresponsive cells may be administered at a dose of between about 100 million to about 200 million cells, about 300 million to about 400 million cells, about 500 million to about 600 million cells, about 700 million to about 800 million cells, or about 900 million to about 1 billion cells, optionally about 500 million to about 1 billion cells, about 2 billion to about 5 billion cells or about 6 billion to about 10 billion cells.

According to the invention the modified immunoresponsive cells may be administered, intravenously, intramuscularly, subcutaneously, topically, orally, transdermally, intraperitoneally, intraorbitally, by implantation, by inhalation, intrathecally, intraventricularly, or intranasally or by intravenous infusion. Preferably, the modified immunoresponsive cells may be administered intravenously or by intravenous infusion.

According to the invention modified immunoresponsive cells can be administered as (a) a single dose in each of one or more dosing cycles,
(b) one or more doses in each of one or more dosing cycles,
(c) a single dose on the first day of each of one or more dosing cycles,
(d) one or more doses in each of one or more dosing cycles comprising a dose on the first day of each of the one or more dosing cycles,
(e) one or more doses in each of one or more dosing cycles, at least one dose being on the first day of each cycle,
(f) a single dose.

According to the invention modified immunoresponsive cells can be administered in a dosing cycle wherein the dosing cycle can be any of 12, 13, 14, 15, 16, 17, 18, 19, 20, 21, 22, 23, 24, 25, 26, 27, 28 weeks or any of 1 month, 2 months, 3 months, 4 months, 5 months, 6 months, 7 months, 8 months, 9 months, 10 months, 11 months, or 12 months, (e.g. since the last previous dose). Accordingly the dosing cycle can be any of 10 to 12 weeks, 11 to 13 weeks, 14 to 17 weeks, 14 to 17 weeks, 18 to 21 weeks, 22 to 24 weeks, 24 to 27 weeks, 28 to 30 weeks, 3 months, 4 months, 5 months, 6 months, (e.g. since the last previous dose).

According to the invention modified immunoresponsive cells can be administered in a dosing cycle wherein the dosing cycle can be on, or commence on or re-commence on:

(a) disease progression following a previous administration of modified immunoresponsive cells, and/or
(b) 12 weeks or more following the previous administration of modified immunoresponsive cells, and wherein
(c) the tumour and/or cancer expresses MAGE-A4 and/or peptide antigen thereof and/or
(d) MAGE-A4 and/or peptide antigen thereof is detected in a subject biological sample and/or is above the normal range.

According to the invention modified immunoresponsive cells can be administered in a dosing cycle wherein the dosing cycle can be on, or commence on or re-commence on:

(a) confirmed response or complete response or partial response following a previous administration of modified immunoresponsive cells, or (b) stable disease for a period of greater than or equal to 2, 3, or 4 months followed by disease progression following the previous administration of modified immunoresponsive cells, and/or
(c) greater than or equal to 12 weeks following the previous administration of modified immunoresponsive cells, and wherein
(c) the tumour and/or cancer expresses MAGE-A4 and/or peptide antigen thereof and/or
(d) MAGE-A4 and/or peptide antigen thereof is detected in a subject biological sample and/or is above the normal range.

The tumour and/or cancer may express MAGE-A4 and/or peptide antigen thereof at a level greater than or equal to an intensity of 1+ in and/or antigen expression frequency by immunohistochemistry of, greater than or equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% preferably greater than or equal to 30 or 32% of tumour and/or cancer cells as determined by immunohistochemistry. The subject biological sample MAGE-A4 and/or peptide antigen thereof which is above the normal range may be greater than or equal to 10, 20, 30, 40, 50, 60, 70, 80, 90, 100, 150, 200, 250, 300, 350, 400, 450 or 500 ng/ml, preferably greater than or equal to 50 or 100 ng/ml.

According to the invention the dose may be a fixed dose or a variable dose. For example where more than one dose is administered, i.e. multiple dose, the dose may be fixed or may be variable, for example where more than one dose is administered the dose may be escalated or increased, for example in each dosing cycle, i.e. may be of increasing level of dose, for example in progression, for example 100 million to 500 million to 1 billion to 5 billion to 10 billion cells.

According to the invention the modified immunoresponsive cells are preferably administered as a single dose of between about 5 billion and about 10 billion cells.

According to the invention the modified immunoresponsive cells can administered for a specified period, meaning that the modified immunoresponsive cells dosing cycles can administered for a specified period. The specified period may be any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months, preferably 24 months.

According to the invention the method may comprise the steps wherein (a) the the modified immunoresponsive cells are administered as a single dose,
(b) the status of disease is determined at a period after the modified immunoresponsive cells administration and compared to the status prior to the modified immunoresponsive cells administration, wherein if progressive disease is determined then,
(c) modified immunoresponsive cells are administered as a single dose, optionally wherein the tumour and/or cancer expresses MAGE-A4 and/or peptide antigen thereof and/or MAGE-A4 and/or peptide antigen thereof is detected in a subject biological sample and/or is above the normal range. Preferably the period is greater than or equal to any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 weeks, preferably greater than or equal to 12 weeks According to the invention the method may comprise the steps wherein (a) the modified immunoresponsive cells are administered as a single dose,
(b) the status of disease is determined at a first and a later second period after the modified immunoresponsive cells administration and compared to the status prior to the modified immunoresponsive cells administration, wherein if stable disease is determined after the first period and progressive disease is determined after the second period then,
(c) modified immunoresponsive cells are administered administered as a single dose, optionally wherein the tumour and/or cancer expresses MAGE-A4 and/or peptide antigen thereof and/or MAGE-A4 and/or peptide antigen thereof is detected in a subject biological sample and/or is above the normal range. Preferably the first period is greater than or equal to any one of 1, 2, 3, 4, 5, 6, 7, 8, months, preferably greater than or equal to 4 months. Preferably the second period is greater than or equal to any one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 months after the first period, preferably greater than or equal to 4 months.

According to the invention a “complete response” (CR) is determined where all target lesions or tumours have been assessed or measured as having disappeared. “Partial response” (PR) is determined when there is a measurement of an at least a 30% decrease in the sum of the longest diameters (SLD) of target lesions or tumours, for example as referenced to the control or pre-treatment comparator. “Progressive disease” (PD) is determined when there is a measurement of at least a 20% increase in the sum of the longest diameters (SLD) of target lesions or tumours, for example as referenced to the control or pre-treatment comparator, since the treatment started or the presence of one or more new lesions. “Stable disease” (SD) is determined where it is determined that there is neither sufficient reduction or decrease in the sum of the longest diameters (SLD) of target lesions or tumours to qualify for PR, nor sufficient increase to qualify for PD, taking as reference the smallest SLD since the treatment started.

According to the present invention the subject prior to treatment can comprise tumour and/or cancer cell MAGE- A4 and/or peptide antigen thereof expression of greater than or equal to an intensity of 1+ in and/or antigen expression frequency by immunohistochemistry of, greater than or equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% preferably greater than or equal to 30 or 32% of tumour and/or cancer cells as determined by immunohistochemistry and non-cancerous MAGE-A4 and/or peptide antigen thereof expression is less than or equal to 1,2, 3, 5, 6, 7, 8, 9, 10% preferably less than or equal to 1% or 5% of cells for non-cancerous or non-tumour tissue at any intensity by immunohistochemistry.

According to the present invention the subject prior to treatment can comprise a biological sample level MAGE-A4 and/or peptide antigen thereof of greater than or equal to 10, 25, 50, 100, 200, 300 or 400 ng/ml preferably greater than or equal to 50 ng/ml and MAGE-A4 expression is less than or equal to 1, 2, 3, 5, 7, 9% or less than 10% preferably less than or equal to 1 or 5% of cells for non-cancerous or non-tumour tissue at any intensity by immunohistochemistry.

According to the present invention the subject prior to treatment may comprise an Eastern Cooperative Oncology Group (ECOG) of 0 to 1 and/or measurable disease (head and neck or lung cancer) according to Response Evaluation Criteria in Solid Tumors (RECIST) 1.1 and/or histologically confirmed head and neck or lung cancer/tumour.

According to the present invention the subject prior to treatment is determined to be HLA-A*02 positive and/or the subject's cancer or tumor shows expression of the MAGE-A4 and/or peptide antigen thereof, for example expression of MAGE-A4 RNA or protein, preferably as herein above described.

According to the present invention if prior to treatment the subject has any one or more of:

(a) HLA-A genotype is HLA-A*02:05 positive,
(b) HLA-A genotype is HLA-A*02:07 as the sole HLA-A*02 allele (eg. a subject with HLA alleles A*02:04 and A*02:07 is eligible),
(c) HLA-A genotype is HLA-A* of any A*02 null allele as the sole HLA-A*02 allele, or
(d) symptomatic CNS metastases, then the subject is not eligible for treatment.

According to the present invention the subject can be positive for HLA-A*02, for example selected from HLA-A*02:01, HLA-A*02:02, HLA-A*02:03, HLA-A*02:04, HLA-A*02:06, HLA-A*02:642 or HLA-A*02:07, preferably HLA-A*02:01 or HLA-A*02:642 and/or the head and neck or lung cancer and/or tumour expresses MAGE-A4 a peptide antigen of MAGE-A4, a peptide antigen of MAGE-A4 comprising GVYDGREHTV, SEQ ID NO: 2.

According to the invention the subject can be intolerant to a standard of care treatment, preferably as described herein, additionally or alternatively the subject and/or the cancer and/or tumour can have been previously unsuccessfully treated with a standard of care treatment, or been previously unsuccessfully treated with any of surgery (resection), radiation therapy, targeted therapy, immunotherapy or chemotherapy or concomitant chemotherapy with surgery (resection), radiation therapy, radiation therapy targeted therapy, or immunotherapy; or been previously unsuccessfully treated with locoregional therapy optionally selected from chemical and/or thermal percutaneous ablation and intraarterial chemoembolotherapy.

According to the present invention the cancer which is head and neck or lung cancer and/or tumour can be primary cancer, secondary cancer, relapsed cancer or refractory cancer or recurrent cancer or locally recurrent cancer, advanced or locally advanced or metastatic cancer, non-resectable cancer or locally confined, cancer with no surgical or radiotherapy option or inoperable cancer, cancer which is not amenable to transplant or loco-regional therapy or any combination thereof. The subject may have relapsed cancer or refractory cancer or recurrent cancer or locally recurrent cancer or metastatic cancer or locally confined or inoperable cancer, or any combination thereof.

Preferably the head and neck cancer and/or tumour is inoperable and/or metastatic and/or advanced and/or locally advanced head and neck cancer or squamous cell head and neck cancer or head and neck squamous cell carcinoma (HNSCC), preferably inoperable or metastatic or advanced or locally advanced HNSCC.

Preferably the lung cancer and/or tumour is inoperable and/or metastatic and/or advanced and/or locally advanced and/or recurrent lung cancer which may be NSCLC or squamous cell NSCLC, adenosquamous NSCLC or large cell carcinoma. Adenosquamous carcinoma of the lung (ASC) is a subtype of non-small-cell lung cancer (NSCLC), containing components of lung adenocarcinoma (ADC) and lung squamous cell carcinoma (SCC). Squamous cell lung cancer, or squamous cell carcinoma of the lung, is one type of non-small cell lung cancer (NSCLC).

There is further provided the treatment method or use according to the invention wherein the subject has not received prior treatment for head and neck or lung cancer and/or tumour, alternatively wherein the subject has received prior treatment for head and neck or lung cancer and/or tumour and/or has failed to respond to the prior treatment.

According to the invention the prior treatment can comprise systemic and/or local therapy, for example any one or more of; surgery, radiation therapy, cryotherapy, laser therapy, topical therapy, chemotherapy, hormonal therapy, targeted drugs, or immunotherapy. Accordingly, the prior treatment can comprise local therapy, for example any one or more of surgery, radiation therapy cryotherapy, laser therapy, topical therapy and/or systemic therapy, for example any one or more of chemotherapy, hormonal therapy, targeted drugs, or immunotherapy. According to the invention the prior treatment can comprise any one of; systemic therapy for initial diagnosis of locoregional disease, systemic therapy after diagnosis of recurrent or metastatic disease, systemic therapy after oligometastatic disease, or systemic therapy after locally recurrent disease.

Accordingly where the treatment is of lung cancer and/or tumour the prior treatment can comprise EGFR inhibitor or ALK tyrosine kinase inhibitor treatment and/or where the cancer or tumour is demonstrated to have EGFR mutation or ALK gene rearrangement the prior EGFR inhibitor or ALK tyrosine kinase inhibitor treatment failed, for example due to progressive disease or unacceptable toxicity or intolerance. Alternatively, where the cancer or tumour is demonstrated to have ROS-1 positive expression prior ALK inhibitor treatment, for example crizotinib treatment, failed, for example due to progressive disease or unacceptable toxicity or intolerance. Accordingly where the treatment is of lung cancer and/or tumour the prior treatment can comprise any of, platinum-based chemotherapy, such as cisplatin or carboplatin; or gemcitabine, paclitaxel, nab-paclitaxel docetaxel, pemetrexed, topotecan, irinotecan, etoposide, vinorelbine or combination thereof with platinum-based chemotherapy, such as cisplatin or carboplatin; or a tyrosine kinase inhibitor or epidermal growth factor receptor (EGFR) inhibitor, such as crizotinib, erlotinib, gefitinib and afatinib, or an immune checkpoint inhibitor, such as pembrolizumab or nivolumab, or monoclonal antibody against nuclear factor kappa-B ligand, such as denosumab; optionally for example which prior treatment failed, for example due to progressive disease or unacceptable toxicity or intolerance.

Accordingly where the treatment is of head and neck cancer and/or tumour the prior treatment can comprise a relevant standard of care as described herein, for treatment of primary tumor in adjuvant, locally advanced, or metastatic settings, for example which failed, for example due to progressive disease or unacceptable toxicity or intolerance. Accordingly where the treatment is of head and neck or lung cancer and/or tumour the prior treatment can comprise a systemic platinum containing chemotherapy, which may be selected from cisplatin or carboplatin chemotherapy, for treatment of primary tumor in adjuvant, locally advanced, or metastatic settings, for example which failed, for example due to progressive disease or unacceptable toxicity or intolerance. Accordingly where the treatment is of head and neck cancer and/or tumour the prior treatment can comprise any of, platinum-based chemotherapy, such as cisplatin or carboplatin; a combination of paclitaxel and carboplatin; docetaxel or combination of docetaxel with cisplatin and/or fluorouracil; an immune checkpoint inhibitor, such as pembrolizumab or nivolumab, optionally on or after platinum-based chemotherapy; a targeted therapy or targeted antibody therapy, such as cetuximab, bevacizumab or erlotinib, or combination of cetuximab with conventional chemotherapy cisplatin or with a platin or 5-fluorouracil; optionally for example which prior treatment failed, for example due to progressive disease or unacceptable toxicity or intolerance.

According to the invention the prior treatment can comprise a PD-1 axis binding antagonist, PD-L1 binding antagonist or PD-1 binding antagonist. Accordingly the prior treatment can comprise (a) an anti-PD-L1 antibody which inhibits binding between PD-L1 and PD-1 and/or between PD-L1 and B7-1,
(b) an anti-PD-L1 antibody which inhibits PD-L1 on the cancer cell surface from transducing a signal to the intracellular pathway,
(c) an anti-PD-1 antibody which inhibits binding between PD-L1 and PD-1 and/or between PD-L2 and PD-1,
(d) an anti-PD-1 antibody which inhibits PD-1 on the T cell surface from transducing a signal to the intracellular pathway,
(e) a PD-L1 binding antagonist which is selected from;
  (i) Durvalumab, Imfinzi or MEDI4736,
  (ii) Atezolizumab, Tecentriq or MPDL3280A,
  (iii) Avelumab, Bavencio or MSB0010718C,
  (iv) MDX-1105, BMS-936559,
(f) a PD-1 binding antagonist is selected from;
  (i) Pembrolizumab, Keytruda, Lambrolizumab or MK-3475,
  (ii) Cemiplimab, Libtayo, or REGN-2810,
  (iii) BMS/ONO, Nivolumab, Opdivo, ONO-4538, BMS-936558 or MDX1106.

According to the invention the prior treatment may comprise an Epidermal Growth Factor Receptor Antagonist, optionally Cetuximab. According to the invention when the prior treatment comprises chemotherapy this may comprise one or more platinum compound, optionally selected from Lipoplatin, Cisplatin, Carboplatin, Oxaliplatin, Nedaplatin, Triplatin tetranitrate, Phenanthriplatin, Satraplatin, Picoplatin. Additionally or alternatively when the prior treatment comprises chemotherapy this may comprise one or more chemotherapeutic agent selected from, methotrexate, capecitabine, taxane, anthracycline, paclitaxel, docetaxel, paclitaxel protein bound particles, doxorubicine, epirubicine, 5-fluorouracil, cyclophosphamide, afatinib, vincristine, etoposide or combinations thereof. Additionally, or alternatively when the prior treatment comprises chemotherapy this may comprise one or more chemotherapeutic agent selected from, FEC: 5-fluorouracil, epirubicine, cyclophosphamide; FAC: 5-fluorouracil, doxorubicine, cyclophosphamide; AC: doxorubicine, cyclophosphamide; EC: epirubicine, cyclophosphamide. According to the invention the prior treatment can comprise any one or more of Sorafenib, a PD1 or PD-L1 antagonist or inhibitor, Regorafenib, Cabozantinib, Sunitinib Brivanib, Everolimus, Tivantinib, Linifanib, or locoregional therapy optionally selected from chemical and/or thermal percutaneous ablation and intraarterial chemoembolotherapy.

According to the invention the subject may not have received prior treatment in recurrence less than or equal to 12 months since the last treatment or less than or equal to 6 months since the last treatment. According to the invention the subject may have not received any prior adjuvant therapy (surgery followed by radiation and/or chemotherapy) in recurrence less than or equal to 12 months since the last treatment or in recurrence less than or equal to 6 months since the last treatment.

According to the invention the treatment extends or improves or effectively extends or effectively improves:

(a) progression free survival,
(b) time to progression,
(c) duration of response,
(d) overall survival,
(e) objective response or objective response rate,
(f) overall response or overall response rate,
(g) partial response or partial response rate,
(h) complete response or complete response rate;
(i) stable disease rate or median stable disease
(j) median progression free survival,
(k) median time to progression,
(l) median duration of response, or
(m) median overall survival;
(n) median objective response or median objective response rate,
(o) median overall response or median overall response rate,
(p) median partial response or median partial response rate,
(q) median complete response or median complete response,
(r) median stable disease rate or median stable disease, in comparison to a control such as in comparison to a placebo treatment or in comparison to prior to treatment or in comparison to without treatment or in comparison to treatment comprising a standard of care as herein described.

According to the invention the treatment extends or improves or effectively extends or effectively improves any one or more of:

(a) Best Overall Response (BOR), (b) Time to Confirmed Response (TTR), (c) Duration of Response (DoR), (d) Duration of Stable Disease (DoSD), (e) Progression Free Survival (PFS), or (f) Overall Survival (OS); in comparison to a control such as in comparison to a placebo treatment or in comparison to prior to treatment or in comparison to without treatment or in comparison to treatment comprising a standard of care as herein described.

Best Overall Response (BOR), can be defined as the best response recorded from the date of T cell infusion until disease progression. Time to Confirmed Response (TTR), can be defined as the duration between T cell infusion and the initial date of the confirmed response. Duration of Response (DoR), can be defined as the duration from the initial date of the confirmed response to the date of PD, progressive disease (or death). Duration of Stable Disease (DoSD), can be defined as the duration from the date of T cell infusion to the date of PD, progressive disease (or death). Progression Free Survival (PFS), can be defined as the interval between the date T cell infusion and the earliest date of disease progression based on RECIST v1.1 or death due to any cause. Overall Survival (OS), can be defined the duration between T cell infusion and death due to any cause.

"Progression free survival" (PFS) refers to the time from treatment (or randomization) to first disease progression or death. "Time to progression" (TTP) does not count patients who die from causes other than the cancer or tumour being treated but is otherwise equivalent to PFS. "Duration of response" (DoR), is the length of time that cancer, tumour or lesion continues to respond to treatment without growing or spreading. According to the invention DOR, TTP and PFS can be assessed by Response Evaluation Criteria in Solid Tumours (RECIST) or can be assessed by CA-125 levels (cancer antigen 125) as a determinant of progression or optionally by reference to the disease biomarkers or expression of MAGE-A4, i.e. MAGE-A4 protein, peptide or mRNA in subject biological sample, cancer and/or tumour tissue or cells. Response durations, rates, readouts, measures or time points may be measured from the day on which a treatment commences for example the day on which the modified immunoresponsive cells are administered to the subject, or the day of administration of the standard of care or placebo.

According to the invention PFS and/or TTP and/or DoR, or median thereof, can be extended or improved by at least 1, 2, 3, or 4 weeks, 1 month, 2 months, 2.3 months, 2.5 months, 2.9 months, 3 months, 3.5 months, 3.8 months, 4 months, 4.5 months, 5 months, 6 months, 7 months, 8 months, 9 months, 10 months, 11 months, 12 months, 16 months, 18 months, 20 months, 22 months, 2 years, 3 years, 4 years, 5, years, 6 years, 7 years, 8 years, 9 years, 10 years in comparison to placebo treatment or in comparison to prior to treatment or in comparison to without treatment or in comparison to treatment comprising a standard of care for example as described herein (control).

In one embodiment, the PFS and/or TTP and/or DoR, or median thereof, is extended about 2.9 months to 3.8 months compared to a control. In one embodiment, the PFS and/or TTP and/or DoR, or medians thereof, is extended at least about 3.8 months compared to a control. In another embodiment, the PFS and/or TTP and/or DoR, or median thereof, is extended by about 2.3 months, in one embodiment, the PFS and/or TTP and/or DoR, or median thereof, is extended about 6 months in comparison to placebo treatment or in comparison to prior to treatment or in comparison to without treatment or in comparison to treatment comprising a standard of care for example as described herein (control).

"Overall survival" refers to a subject remaining alive for a defined period of time. According to the invention the overall survival, or median thereof, is improved or extended by about or greater than any of about 1 month, 2 months, 2.3 months, 2.5 months, 2.9 months, 3 months, 3.5 months, 3.8 months, 4 months, 4.5 months, 5 months, about 6 months, about 7 months, about 8 months, about 9 months, about 10 months, about 11 months, about 12 months, about 1.5 years, about 2 years, about 3 years, about 4 years, about 5 years, about 6 years, about 7 years, about 8 years, about 9 years, about 10 years, from initiation of the method or treatment according to the invention or from initial diagnosis, optionally the event used for survival analysis can be death from any cause. "Survival" refers to a subject remaining alive and includes progression free survival (PFS) and overall survival (OS). "Overall survival" is the length of time from either the date of diagnosis or the start of treatment for the disease, tumour and/or cancer, that subjects diagnosed with the disease are still alive. Survival can be estimated by the Kaplan-Meier method, and any differences in survival are computed using the stratified log-rank test; "extending survival" or "increasing the likelihood of survival" is meant increasing PFS and/or OS in a treated subject in comparison to placebo treatment or in comparison to prior to treatment or in comparison to without treatment or in comparison to treatment comprising a standard of care for example as described herein. According to the invention overall survival or survival can be extended or improved by at least any of about, 1 month, 2 months, 2.3 months, 2.5 months, 2.9 months, 3 months, 3.5 months, 3.8 months, 4 months, 4.5 months, 5 months, 6 months, 7 months, 8 months, 9 months, 10 months, 11 months, 12 months, 16 months, 18 months, 20 months, 22 months, 2 years, 3 years, 4 years, 5, years, 6 years, 7 years, 8 years, 9 years, 10 years in comparison to placebo treatment or in comparison to prior to treatment or in comparison to without treatment or in comparison to treatment comprising a standard of care (a control).

"Objective response rate" (ObRR) is the proportion of subjects with tumour size reduction of a predefined amount, optionally determined by sum of the longest diameters (SLD) of target lesions or tumours, and for a minimum time period. "Overall response rate (ORR)" is defined as the proportion of subjects who have a partial or complete response to therapy; it does not include stable disease. ORR is generally defined as the sum of complete responses (CR) and partial responses (PRs) over a specified time period. According to the invention ObRR and/or ORR and/or PR and/or CR and/or SD can be extended or improved by at least 5%, 10%, 15%, 20%, 25%, 30%, 35%, 40%, 45%, 50%, 55%, 60%, 65%, 70%, 75%, 80%, 85%, 90%, 95%, in comparison to placebo treatment or in comparison to prior to treatment or in comparison to without treatment or in comparison to treatment comprising a standard of care for example as described herein.

According to the present invention, the method may further comprise determining the expression level of a biomarker in a sample, biological sample, from the subject wherein the level of the biomarker is compared to a reference level in order to determine the subject's likelihood to respond to the treatment or to determine the subject's level of response to the treatment, wherein the sample is obtained either before during or after the treatment. The reference level may be the level prior to treatment of the subject or may be the level associated with the presence of cancer or the lack of presence of cancer. The biomarker may be a T-effector-associated gene, for example CD8A, perforin (PRF1), granzyme A (GZMA), granzyme B (GZMB), interferon-γ (IFN-v), CXCL9, or CXCL10. The biomarker may be an activated stroma-associated gene, for example transforming growth factor-β (TGF-β), fibroblast-activated protein (FAP), podplanin (PDPN), a collagen gene, or biglycan (BGN). The biomarker may be a or a myelokJ-derived suppressor cell-associated gene, for example CD68, CD163, FOXP3, or androgen-regulated gene 1. Alternatively, the biomarker may be PD-L1, CD8, or androgen receptor (AR)

gene. Alternatively, the biomarker may be a disease biomarker as herein before described.

According to the present invention the subject undergoes lymphodepleting chemotherapy prior to administration of the modified immunoresponsive cells expressing or presenting a heterologous T-cell receptor (TCR). The lymphodepleting chemotherapy may comprise administration of cyclophosphamide and/or fludarabine. Preferably the cyclophosphamide is administered at a dose of about 100, 150, 200, 250, 300, 350, 400, 450, 500, 550, 600, 650, 700, 750, 800 or 850 mg/m$^2$/d [d=day], preferably about 500 or 600 mg/m$^2$/d, preferably wherein the administration is for 1 day, 2 days (×2d), 3 days (×3d), 4 days (×4d) or 5 days (×5d). Preferably the fludarabine is administered at a dose of about 5, 10, 15, 20, 25, 30, 35, 40, 450, 50, 55, 60, 65, 70, 75, 80 or 85 mg/m$^2$/d, preferably wherein the administration is for 1 day, 2 days (×2d), 3 days (×3d), 4 days (×4d) or 5 days (×5d). Preferably the lymphodepleting chemotherapy comprises administration of cyclophosphamide and fludarabine optionally at a dose of 500 mg/m$^2$/d×3d cyclophosphamide and 20 mg/m$^2$/d×3d fludarabine or at a dose of 600 mg/m$^2$/d×3d cyclophosphamide and 30 mg/m$^2$/d×4d.

According to the invention the lymphodepleting chemotherapy can administered at 3, 4, 5, 6, 7, 8, 9, 10 days preferably 7 to 5 or 7 to 4 days prior to administration of the modified immunoresponsive cells expressing or presenting a heterologous T-cell receptor (TCR). The administration of cyclophosphamide and fludarabine may be sequential separate or simultaneous, the administration may be administered intravenously or by intravenous infusion.

The invention further provides a method of (a) reducing subject MAGE-A4 expression or concentration, for example in a subject biological sample,
(b) enhancing immune function,
(c) reducing tumour growth or tumour growth rate or maintaining tumour size after cessation of treatment or reducing tumour number or tumour burden,
(d) increasing serum cytokine and/or interferon level or concentration,
(e) improving T-cell persistence,
(f) improving T-cell infiltration of tumour,
(g) inducing a change in disease biomarker indicative of effective treatment of head and neck or lung cancer and/or tumour, in a subject having head and neck or lung cancer and/or tumour comprising administering to the subject treatment regimen comprising an effective amount of modified immunoresponsive cells expressing or presenting a heterologous T-cell receptor (TCR) which binds MAGE-A4 or a peptide antigen of MAGE-A4 or a peptide antigen of MAGE-A4 comprising GVYDGREHTV, SEQ ID NO: 2, as herein before described with reference to the method of treatment and the aspects and embodiments and features relating thereto, optionally in comparison to prior to treatment or treatment with placebo or without treatment or treatment comprising a standard of care as described herein.

Accordingly, the invention provides a method of enhancing immune function wherein:

(a) CD8 T cells in the subject have enhanced priming, activation, proliferation and/or cytolytic activity,
(b) the number of CD8 T cells is elevated in the subject,
(c) the cancer and/or tumour cells in the subject selectively have elevated expression of MHC class I antigen expression, optionally wherein PBMC cells of the subject do not have elevated expression of MHC class I antigen,
(d) the antigen presenting cells in the subject have enhanced maturation and activation, optionally wherein the antigen presenting cells are dendritic cells,
(e) the serum levels of IL-10 and/or IL-8 in the subject are reduced,
(f) the cancer and/or tumour of the subject has elevated levels of T-cell infiltration,
(g) the T cells of the subject have reduced levels of T-cell PD-1 expression; respectively in a subject having head and neck or lung cancer and/or tumour comprising administering to the subject treatment regimen comprising an effective amount of modified immunoresponsive cells expressing or presenting a heterologous T-cell receptor (TCR) which binds MAGE-A4 or a peptide antigen of MAGE-A4 or a peptide antigen of MAGE-A4 comprising GVYDGREHTV, SEQ ID NO: 2, as herein before described with reference to the method of treatment and the aspects and embodiments and features relating thereto, optionally in comparison to prior to treatment or treatment with placebo or without treatment or treatment comprising a standard of care as described herein.

Accordingly with reference to the foregoing and the subject treated (a) the CD8 T cell activation may be characterised by an elevated frequency of gamma-IFN$^+$CD8 T cells and/or enhanced cytolytic activity; (b) the maturation of the antigen presenting cells may be characterised by increased frequency of CD83$^+$ dendritic cells; (c) the activation of the antigen presenting cells may be characterised by elevated expression of CD80 and CD86 on dendritic cells; (d) the CD8 T cell may be an antigen-specific CD8 T cell.

According to the invention there is provided;

(a) a kit comprising comprising an effective amount of modified immunoresponsive cells expressing or presenting a heterologous T-cell receptor (TCR) which binds MAGE-A4 or a peptide antigen of MAGE-A4 or a peptide antigen of MAGE-A4 comprising GVYDGREHTV, SEQ ID NO: 2, and a package insert comprising instructions for using the modified immunoresponsive cells to treat or delay the progression of head and neck or lung cancer and/or tumour in a subject,
(b) a kit comprising comprising an effective amount of modified immunoresponsive cells expressing or presenting a heterologous T-cell receptor (TCR) which binds MAGE-A4 or a peptide antigen of MAGE-A4 or a peptide antigen of MAGE-A4 comprising GVYDGREHTV, SEQ ID NO: 2 and a package insert comprising instructions for using the modified immunoresponsive cells in a method of
    (i) reducing subject MAGE-A4 expression or concentration, for example in a subject biological sample,
    (ii) enhancing immune function,
    (iii) reducing tumour growth or tumour growth rate or maintaining tumour size after cessation of treatment or reducing tumour number or tumour burden,
    (iv) increasing serum cytokine and/or interferon level or concentration,
    (v) improving T-cell persistence,
    (vi) improving T-cell infiltration of tumour, or
    (vii) inducing a change in disease biomarker indicative of effective treatment of head and neck or lung cancer and/or tumour, in a subject having cancer and/or tumour as herein before described.

Further Aspect of Invention

According to a further aspect, the present invention additionally provides a method of treating, preventing or delaying the progression of cancer and/or tumour in a subject comprising administering to the subject a treatment regimen comprising an effective amount of modified immunoresponsive cells expressing or presenting a heterologous T-cell receptor (TCR) or chimeric antigen receptor (CAR) which binds MAGE-A4 (SEQ ID NO: 1), a peptide antigen of MAGE A4, optionally comprising GVYDGREHTV, SEQ ID NO: 2, wherein the cancer and/or tumour is any one of (a) ovarian cancer and/or tumour, (b) urothelial/bladder cancer and/or tumour, (c) melanoma, or (d) sarcoma or synovial sarcoma.

Where cancer and/or tumour is preferably advanced and/or metastatic and/or inoperable, sarcoma, optionally soft tissue sarcoma, optionally synovial or myxoid round cell liposarcoma.

According to the further aspect, the heterologous TCR or CAR may bind specifically and/or selectively to MAGE-A4 (SEQ ID NO: 1), a peptide antigen of MAGE A4 or a peptide antigen of MAGE A4 comprising GVYDGREHTV, SEQ ID NO: 2.

According to the further aspect, the MAGE-A4 (SEQ ID NO: 1), the peptide antigen of MAGE A4 or the peptide antigen of MAGE A4 comprising GVYDGREHTV, SEQ ID NO: 2 may be associated with any one of (a) ovarian cancer and/or tumour, (b) urothelial/bladder cancer and/or tumour, or (c) melanoma cancer and/or tumour (d) sarcoma or synovial sarcoma, and/or is presented by tumour and/or cancer cell or tissue. Accordingly the (a) ovarian cancer and/or tumour, (b) urothelial/bladder cancer and/or tumour, (c) melanoma cancer and/or tumour, or (d) sarcoma or synovial sarcoma may be a MAGE A4 expressing cancer and/or tumour, and/or expresses MAGE A4 or a peptide antigen thereof or a peptide antigen of MAGE A4 comprising GVYDGREHTV, SEQ ID NO: 2.

According to the further aspect, the peptide antigen of MAGE-A4 or peptide antigen of MAGE A4 comprising GVYDGREHTV, SEQ ID NO: 2 may be complexed with a peptide presenting molecule, optionally major histocompatibility complex (MHC) or human leukocyte antigen (HLA), optionally class I or class II, optionally selected from HLA*02, HLA-A*02:01, HLA-A*02:02, HLA-A*02:03, HLA-A*02:04, HLA-A*02:06, HLA-A*02:642 or HLA-A*02:07, preferably HLA-A*02:01 or HLA-A*02. Preferably the heterologous TCR binds specifically and/or selectively to the peptide antigen and/or the peptide presenting molecule and/or complex thereof. Alternatively and according to the further aspect, the MAGE A4 or a peptide antigen thereof or a peptide antigen of MAGE A4 comprising GVYDGREHTV, SEQ ID NO: 2 may be presented independently of a peptide presenting molecule.

According to the further aspect, the heterologous TCR may comprise a TCR alpha chain variable domain and a TCR beta chain variable domain, wherein:

(i) the alpha chain variable domain comprises CDRs having the sequences VSPFSN (αCDR1), SEQ ID NO:11 or amino acids 48-53 of SEQ ID NO:5, or sequence having at least 50% sequence identity thereto, LTFSEN (αCDR2), SEQ ID NO:12 or amino acids 71-76 of SEQ ID NO:5, or sequence having at least 50% sequence identity thereto, and CVVSGGTDSWGKLQF (αCDR3), SEQ ID NO:13 or amino acids 111-125 of SEQ ID NO:5, or sequence having at least 50% sequence identity thereto, and (ii) the beta chain variable domain comprises CDRs having the sequences KGHDR (βCDR1), SEQ ID NO:14 or amino acids 46-50 of SEQ ID NO:7, or sequence having at least 50% sequence identity thereto, SFDVKD (βCDR2), SEQ ID NO:15 or amino acids 68-73 of SEQ ID NO:7, or sequence having at least 50% sequence identity thereto, and CATSGQGAYEEQFF (βCDR3), SEQ ID NO:16 or amino acids 110-123 of SEQ ID NO:7 or sequence having at least 50% sequence identity thereto, Accordingly the heterologous TCR may comprise a TCR in which (a) the alpha chain variable domain comprises an amino acid sequence that has at least 80%, identity to SEQ ID NO:9, and/or the beta chain variable domain comprising an amino acid sequence that has at least 80% identity to SEQ ID NO:10, (b) the alpha chain variable domain comprises an amino acid sequence comprising SEQ ID NO: 9, and/or the beta chain variable domain comprises SEQ ID NO:10, (c) the alpha chain comprises an amino acid sequence that has at least 80%, identity to SEQ ID NO: 5, and/or the beta chain comprising an amino acid sequence that has at least 80% identity to SEQ ID NO:6, or (d) the alpha chain comprises an amino acid sequence comprising SEQ ID NO:5, and/or the beta chain comprises an amino acid sequence comprising SEQ ID NO:6.

According to the further aspect, the modified immunoresponsive cells expressing or presenting a heterologous TCR may further express or present a heterologous co-receptor, optionally wherein the co-receptor is a CD8 co-receptor, optionally wherein the heterologous CD8 co-receptor is heterodimer or homodimer, a CD8ab heterodimer or a CD8aa homodimer.

Accordingly the heterologous CD8 co-receptor may comprise;

(a) a CDR 1 of at least 80% sequence identity to amino acid sequence VLLSNPTSG, SEQ ID NO: 17, CDR 2 of at least 80% sequence identity to amino acid sequence YLSQNKPK SEQ ID NO: 18 and CDR 3 of at least 80% sequence identity amino acid sequence LSNSIM SEQ ID NO: 19, (b) a CDR 1 of amino acid sequence VLLSNPTSG, SEQ ID NO:17, CDR 2 of amino acid sequence YLSQNKPK SEQ ID NO:18 and CDR 3 of amino acid sequence LSNSIM SEQ ID NO: 19, (c) an amino acid sequence having at least 80% sequence identity to amino acids number 22 to 235 of SEQ ID NO: 3, or 22 to 135 of SEQ ID NO: 3, or (d) an amino acid sequence having 100% sequence identity to amino acids number 22 to 235 of sequence of SEQ ID NO: 3, or 22 to 135 of SEQ ID NO: 3.

According to the further aspect, the modified immunoresponsive cells expressing or presenting a heterologous CAR or TCR may further express or present one or more heterologous co-stimulatory ligands, optionally 4-1BBL and/or CD80.

According to the further aspect, the modified immunoresponsive cells may be (a) B cells, T cells or natural killer (NK) cells, (b) T cells, optionally $CD4^+$ T cells and/or CD8+ T cells, optionally wherein the modified immunoresponsive cells may be a population of CD4+ T cells; or CD8+ T cells, or a mixed population of CD4+ T cells and CD8+ T cells.

According to the further aspect, the modified immunoresponsive cells can be administered continuously or intermittently.

According to the further aspect, the modified immunoresponsive cells can be administered as multiple doses or is administered as a single dose. Accordingly the single or multiple doses can administered in one or more dosing cycles, optionally wherein the dose may be a fixed dose or a variable dose. The modified immunoresponsive cells can be administered at a dose of between about 500 million to about 1 billion cells, about 2 billion to about 5 billion cells or about 6 billion to about 10 billion cells.

According to the further aspect, the modified immunoresponsive cells can be administered as;

(a) a single dose in each of one or more dosing cycles,
(b) one or more doses in each of one or more dosing cycles,
(c) a single dose on the first day of each of one or more dosing cycles,
(d) one or more doses in each of one or more dosing cycles, at least one dose being on the first day of each cycle,
(e) one or more doses in each of one or more dosing cycles, at least one dose being on the first day of each cycle,
(f) a single dose.

According to the further aspect, where the modified immunoresponsive are administered according to a dosing cycle the dosing cycle may be between 2 and 6 months or on disease progression.

According to the further aspect, where the the modified immunoresponsive are administered according to a dosing cycle the dosing cycle can be on:

(a) disease progression following a previous administration of modified immunoresponsive cells, and 12 weeks or more following the previous administration of modified immunoresponsive cells, and wherein
(b) the tumour and/or cancer expresses MAGE-A4 and/or peptide antigen thereof, and/or
(d) MAGE-A4 and/or peptide antigen thereof, is detected in a subject biological sample and/or is above the normal range.

According to the further aspect, where the the modified immunoresponsive are administered according to a dosing cycle the dosing cycle can be on:

(a) complete or partial response following a previous administration of modified immunoresponsive cells, or (b) stable disease for a period of greater than or equal to 4 months followed by disease progression following the previous administration of modified immunoresponsive cells; and (c) greater than or equal to12 weeks following the previous administration of modified immunoresponsive cells, and wherein
(d) the tumour and/or cancer expresses MAGE-A4 and/or peptide antigen thereof, and/or
(d) MAGE-A4 and/or peptide antigen thereof, is detected in a subject biological sample and/or is above the normal range.

According to the further aspect, the modified immunoresponsive cells may be administered intravenously or by intravenous infusion.

According to the further aspect, prior to treatment the subject may have an Eastern Cooperative Oncology Group (ECOG) of 0 to 1 and/or measurable disease according to Response Evaluation Criteria in Solid Tumors (RECIST) 1.1 and/or histologically confirmed ovarian cancer and/or tumour, urothelial/bladder cancer and/or tumour, or melanoma.cancer/tumour.

According to the further aspect, if prior to treatment the subject has any one or more of:

(a) HLA-A genotype is HLA-A*02:05 positive,
(b) HLA-A genotype is HLA-A*02:07 as the sole HLA-A*02 allele (eg. a subject with HLA alleles A*02:04 and A*02:07 is eligible),
(c) HLA-A genotype is HLA-A* of any A*02 null allele as the sole HLA-A*02 allele, or
(d) symptomatic CNS metastases, then the subject is excluded from the treatment.

According to the further aspect, the subject may be intolerant to a standard of care treatment, optionally systemic platinum-based chemotherapy treatment and/or the ovarian cancer and/or tumour, urothelial/bladder cancer and/or tumour, melanoma.cancer/tumour and/or sarcoma or synovial sarcoma may have been previously unsuccessfully treated with a standard of care treatment, optionally systemic platinum-based chemotherapy treatment.

According to the further aspect, the ovarian cancer and/or tumour, urothelial/bladder cancer and/or tumour, melanoma.cancer/tumour or sarcoma or synovial sarcoma may have been previously unsuccessfully treated with any of surgery (resection), radiation therapy, targeted therapy, immunotherapy or chemotherapy or concomitant chemotherapy with surgery (resection), radiation therapy, radiation therapy targeted therapy, checkpoint inhibitor or immunotherapy.

According to the further aspect, the ovarian cancer and/or tumour, urothelial/bladder cancer and/or tumour, melanoma.cancer/tumour or sarcoma or synovial sarcoma may be; primary cancer, secondary cancer, relapsed cancer or refractory cancer or recurrent cancer or locally recurrent cancer or metastatic cancer, non-resectable cancer or locally confined, cancer with no surgical or radiotherapy option or inoperable cancer optionally wherein the cancer is not amenable to transplant or loco-regional therapy.

According to the further aspect, prior to administration of the modified immunoresponsive cells expressing or presenting a heterologous T-cell receptor (TCR) or CAR the subject may undergo lymphodepleting chemotherapy optionally comprising administration of cyclophosphamide and fludarabine optionally at a dose of 500 $mg/m^2/d \times 3d$ cyclophosphamide and 20 $mg/m^2/d \times 3d$ fludarabine or at a dose of 600 $mg/m^2/d \times 3d$ cyclophosphamide and 30 $mg/m^2/d \times 4d$, further optionally wherein the lymphodepleting chemotherapy is administered 7 to 5 or 7 to 4 days prior to administration of the modified immunoresponsive cells expressing or presenting a heterologous T-cell receptor (TCR) or CAR.

According to the further aspect, the subject may not have received prior treatment for cancer and/or tumour, e.g. treatment naïve; alternatively the subject may have received prior cancer and/or tumour treatment and/or has failed to respond to prior cancer and/or tumour treatment. Accordingly, the prior treatment may comprise any of the following:

(a) systemic and/or local therapy, optionally any one or more of surgery, radiation therapy cryotherapy, laser therapy, topical therapy and/or systemic therapy, for example any one or more of chemotherapy, hormonal therapy, targeted drugs, targeted chemotherapy, or immunotherapy,
(b) a PD-L1 binding antagonist or PD-1 binding antagonist, optionally wherein the PD-1 axis binding antagonist or PD-L1 binding antagonist is an antibody, (c) an Epidermal Growth Factor Receptor Antagonist, optionally Cetuximab, erlotinib, gefitinib or afatinib,
(d) chemotherapy comprising a platinum compound, optionally selected from any of Lipoplatin, Cisplatin, Carboplatin, Oxaliplatin, Nedaplatin, Triplatin tetranitrate, Phenanthriplatin, Satraplatin, Picoplatin,
(e) comprising a chemotherapeutic agent optionally selected from any of, methotrexate, capecitabine, taxane, anthracycline, paclitaxel, docetaxel, paclitaxel protein bound particles, doxorubicine, epirubicine, 5-fluorouracil, cyclophosphamide, afatinib, vincristine, etoposide or combinations thereof.
(f) chemotherapy comprising a chemotherapeutic agent selected from any of, FEC: 5-fluorouracil, epirubicine, cyclophosphamide; FAC: 5-fluorouracil, doxorubicine, cyclophosphamide; AC: doxorubicine, cyclophosphamide; EC: epirubicine, cyclophosphamide.

Where the method or treatment according to the invention is for sarcoma or synovial sarcoma the standard of care may comprise treatment selected from any one or more of or may be selected from any one or more of an anthracycline-based therapy, for example a single agent anthracycline for example doxorubicin, daunorubicin, epirubicin or idarubicin; single agent Ifosfamide; combined anthracycline and Ifosfamide, or combined doxorubicin+Ifosfamide, or any one or more of Pazopanib, Trabectedin, Eribulin, Gemcitabine+/−, Docetaxel, or Dacarbazine.

Where the method or treatment according to the invention is for sarcoma or synovial sarcoma the prior treatment may comprise treatment selected from any one or more of or may be selected from any one or more of an anthracycline-based therapy, for example a single agent anthracycline for example doxorubicin, daunorubicin, epirubicin or idarubicin; single agent Ifosfamide; combined anthracycline and Ifosfamide, or combined doxorubicin+Ifosfamide, or any one or more of Pazopanib, Trabectedin, Eribulin, Gemcitabine+/−, Docetaxel, or Dacarbazine.

According to the further aspect, the subject may not have received prior treatment in recurrence less than or equal to 12 months since the last treatment or less than or equal to 6 months since the last treatment.

According to the further aspect, the subject may not have received any prior adjuvant therapy (e.g. surgery followed by radiation and/or chemotherapy) or locoregional therapy in recurrence less than or equal to 12 months since the last treatment or in recurrence less than or equal to 6 months since the last treatment.

According to the further aspect, the treatment may effectively extend or improve:
(a) progression free survival,
(b) time to progression,
(c) duration of response,
(d) overall survival,
(e) objective response or objective response rate,
(f) overall response or overall response rate,
(g) partial response or partial response rate,
(h) complete response or complete response rate;
(i) stable disease rate or median stable disease
(j) median progression free survival,
(k) median time to progression,
(l) median duration of response, or
(m) median overall survival;
(n) median objective response or median objective response rate,
(o) median overall response or median overall response rate,
(p) median partial response or median partial response rate,
(q) median complete response or median complete response,
(r) median stable disease rate or median stable disease, in comparison to a placebo treatment or in comparison to prior to treatment or in comparison to without treatment or in comparison to treatment comprising a standard of care, optionally systemic platinum-based chemotherapy treatment.

According to the further aspect, the treatment may effectively extend or improve progression free survival (or median thereof) by 20 weeks or more, optionally 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 weeks or more, optionally wherein the median overall survival has not been reached, preferably wherein the method of treating, preventing or delaying the progression of cancer and/or tumour in a subject according to the further aspect is in respect of sarcoma or synovial sarcoma, for example in comparison to a placebo treatment or in comparison to prior to treatment or in comparison to without treatment or in comparison to treatment comprising a standard of care as described herein, optionally in comparison to treatment comprising any one or more of Pazopanib, Trabectedin, Eribulin, Gemcitabine+/−, Docetaxel, or Dacarbazine. Preferably the PFS in respect of the treatment of sarcoma or synovial sarcoma according to the invention or according to the further aspect is 20 weeks or greater, optionally 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 weeks or greater.

According to the further aspect, the treatment may effectively extend or improve ORR overall response rate, preferably wherein the method of treating, preventing or delaying the progression of cancer and/or tumour in a subject according to the further aspect is in respect of sarcoma or synovial sarcoma, for example in comparison to a placebo treatment or in comparison to prior to treatment or in comparison to without treatment or in comparison to treatment comprising a standard of care as described herein, optionally in comparison to treatment comprising any one or more of Pazopanib, Trabectedin, Eribulin, Gemcitabine+/−, Docetaxel, or Dacarbazine. Preferably the ORR is improved 2, 3, 4, 5, 6, 7, 8, 9, 10, 11 fold optionally in comparison to treatment comprising a standard of care as described herein, optionally in comparison to treatment comprising any one or more of Pazopanib, Trabectedin, Eribulin, Gemcitabine+/−, Docetaxel, or Dacarbazine. Preferably the ORR, preferably for treatment of sarcoma or synovial sarcoma according to the invention or further aspect, is a value selected from any of 4%, 5%, 6%, 7%, 8%, 9%, 10%, 15%, 16%, 20%, 25%, 30%, 35%, 40%, 45%, 46%, 50%, 60%, 70%, 80%, 90% or greater, preferably 40% or 42% or 43 or 45% or 46% or 47% or greater. The ORR may for example be the value for the increase in the sum of the longest diameters (SLD) of target lesion or lesions or tumour or tumours of a subject or group of subjects or median value thereof.

According to the further aspect, preferably wherein the method of treating, preventing or delaying the progression of cancer and/or tumour in a subject according to the further aspect is in respect of sarcoma or synovial sarcoma, the treatment may effectively provide a BOR, for example BOR in partial response or stable disease, of any one of 20%, 25%, 30%, 35%, 40%, 45%, 46%, 50%, 60%, 70%, 80%, 90% or greater, preferably 40% or greater, preferably 43% or greater.

According to the further aspect, preferably wherein the method of treating, preventing or delaying the progression of cancer and/or tumour in a subject according to the further aspect is in respect of sarcoma or synovial sarcoma, the treatment may effectively provide a BOR, for example BOR in progressive disease, of any one of 5%, 6%, 7%, 8%, 9%, 10%, 15%, 20%, 25%, 3%, 35%, 40%, 45%, 50% or greater, preferably 6% or greater, preferably 6.3%.

In embodiments, the further aspect comprises a modified immunoresponsive cell expressing or presenting a heterologous T-cell receptor (TCR) or chimeric antigen receptor (CAR) which binds MAGE-A4 (SEQ ID NO: 1), a peptide antigen of MAGE A4, optionally comprising GVYDGREHTV, SEQ ID NO: 2, for use in treating, preventing or delaying the progression of cancer and/or tumour in a subject, wherein the cancer and/or tumour is any one of (a) ovarian cancer and/or tumour, (b) urothelial/bladder cancer and/or tumour, (c) melanoma, or (d) sarcoma or synovial sarcoma.

In certain embodiments of the further aspect, the invention comprises administering to the subject a treatment regimen comprising an effective amount of the immunoresponsive cells.

The invention will be further described by reference to the following figures and examples.

FIGURES

FIG. 1. Table of best overall response: RECIST v1.1, responses in, head & neck cancer, and lung cancer following MAGE-A4$^{c1032}$ T-cell infusion.

FIG. 2. CT data demonstrating a 50% decrease in target lesions in lung cancer at a 12 week period following MAGE-A4$^{c1032}$ T-cell infusion for the cohort subject receiving a 10 billion cell infusion, upper panels showing tumour reduction, lower panels showing fluid reduction in in pleural space.

FIG. 3. Data table showing the % change reduction from baseline lesion SLC i.e. percent changes in sum of diameters in target lesions measurement (Sum of Diameters=Sum of the long diameters for non-nodal lesions and short axis for nodal lesions), responses evaluated by RECIST v1.1.

Figure 4:
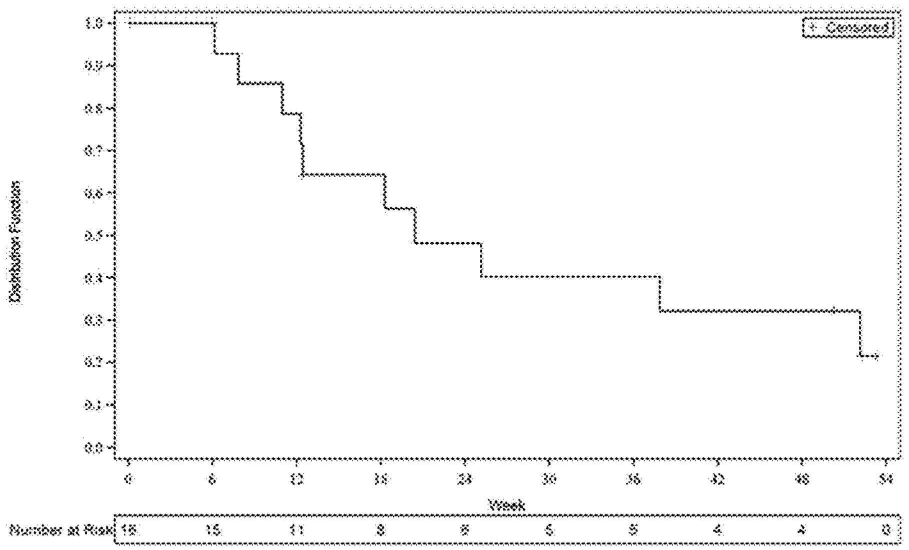
Figure 4:
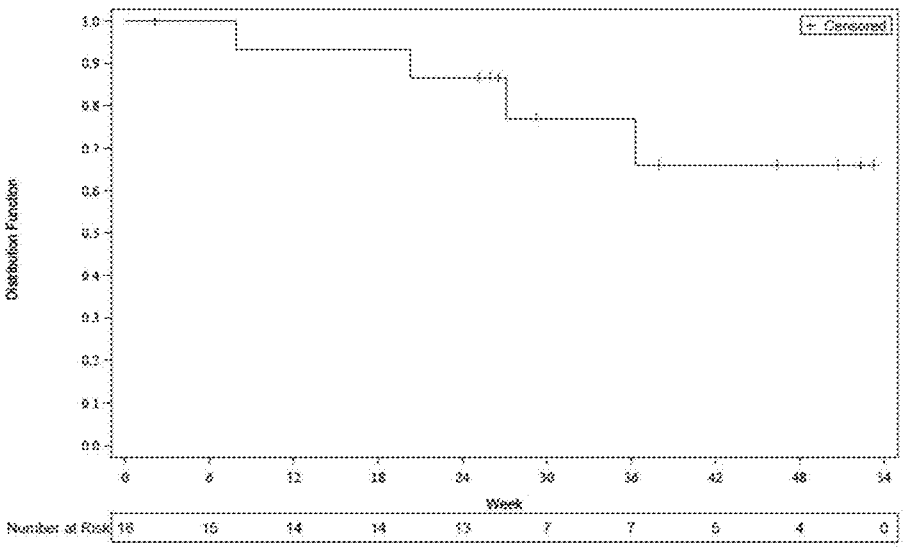

FIG. 4. Figure showing PFS and OS for treatment of sarcoma (synovial sarcoma) with MAGE-A4$^{c1032}$ T-cell infusion.

FIG. 5. Table of best overall response: RECIST v1.1, responses in sarcoma (synovial sarcoma) following MAGE-A4$^{c1032}$ T-cell infusion.

FIG. 6. Comparative efficacy observed in synovial sarcoma treatment; tables of % response rates: RECIST v1.1 percentage change from baseline SLD), responses in sarcoma (synovial sarcoma) following (a) standard of care treatments (b) MAGE-A4$^{c1032}$ T-cell infusion.

Figure 7:
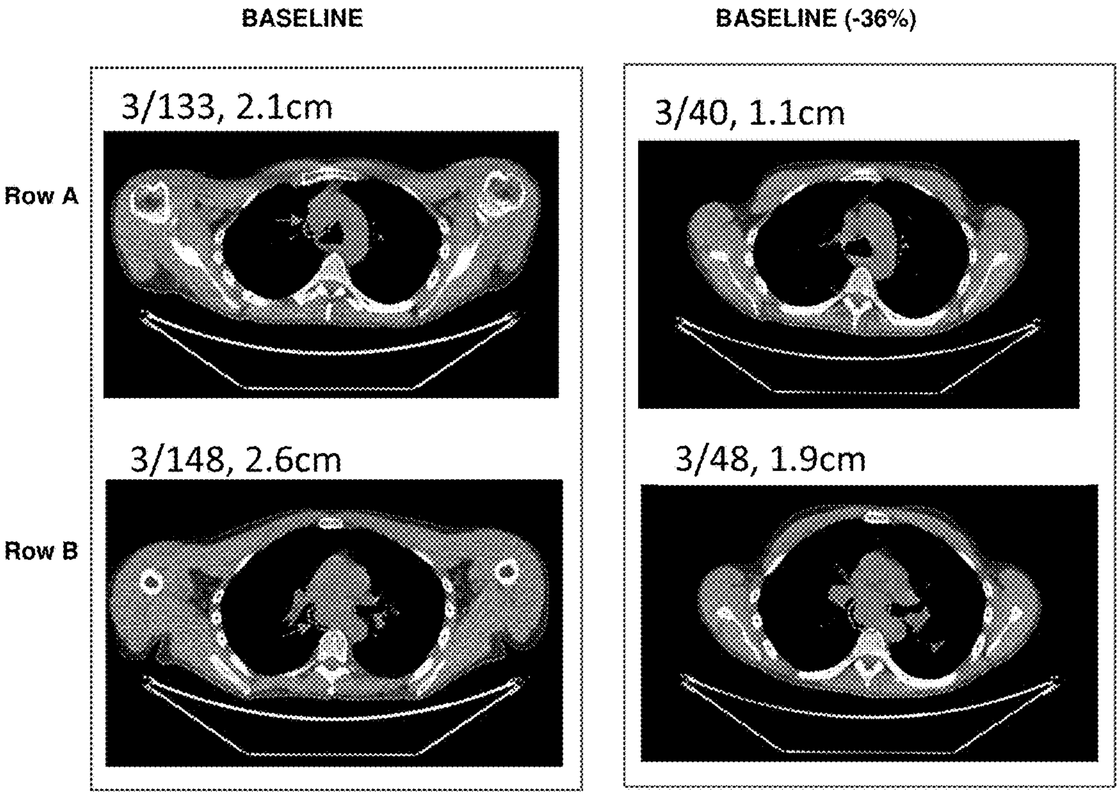

FIG. 7. CT scans showing PR (partial response) at 24 weeks post transduced T cell infusion: CT data (lesion circled) from subject with head and neck cancer with MAGE-A4 expression (biopsy showed invasive SCC and left artenoid SCC.), previous treatment regimens had included: cisplatin, carboplatin+doxetaxel, pembrolizumab. Baseline scan showed SLD 47 mm (LN (lymph node) in chest target lesions & NT lesion in neck). Subject received $3.83\times10^9$ transduced cells by infusion (ADP-A2M4 SPEAR T-cells). Recorded 36% reduction in SLD of lesion from baseline measurement at 24 weeks.

Figure 8:
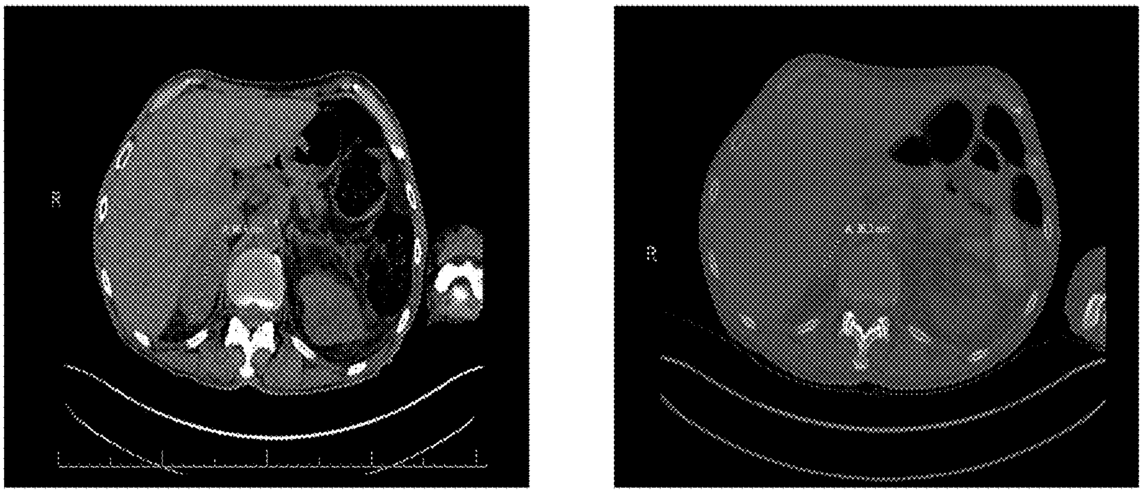

FIG. 8. CT scans showing PR (partial response) for subject with lung cancer at 20 weeks post transduced T cell infusion with tabulated data for the same subject: CT data (lesion with measurement scale) from subject with stage IV squamous cell NSLCL (PD-L1, ROS1). Biopsy showed MAGE-A4 antigen expression [IHC Levels: +1(0%); +2(5%); +3(95%)]. Prior cancer therapy included: surgery, systemic therapy (including chemotherapy, targeted therapy and immunotherapy); carboplatin/paclitaxel/denosumab; nivolumab; nivolumab and ipilimumab; docetaxel and ramucirumab; radiation therapy. Subject was infused with $6.5\times10^9$ transduced T cells (ADP-A2M4 SPEAR T-cells). Recorded 41.7% reduction in SLD of lesion from baseline measurement at 20 weeks.

EXAMPLES

Example 1—A Phase I Open Label, Clinical Trial Evaluating the Safety and Anti-tumour Activity of Autologous T Cells Expressing Enhanced TCRs Specific for MAGE-A4, MAGE-A4$^{c1032}$T in HLA-A2+subjects with MAGE-A4 positive head and neck and lung tumors.

Methods

The following presents an in human study of genetically engineered MAGE-A4$^{c1032}$T cells in subjects with HLA-A*02 and MAGE-A4 positive inoperable locally advanced or metastatic tumors for head and neck or lung cancer.

Disease was histologically or cytogenetically confirmed and/or measurable disease recorded according to RECIST v1.1 criteria. Subjects who were eligible based on HLA type and who met MAGE-A4 criteria were screened for general health, performance status and disease stage. Following Screening, subjects meeting all eligibility criteria underwent leukapheresis to obtain cells for the manufacture of autologous MAGE-A4 TCR bearing T-cells. Eligible subjects had an ECOG Performance Status 0-1, adequate organ function and measurable disease required prior to lymphodepletion and:

(a) Inoperable or metastatic (advanced) squamous cell head and neck cancer. Has received a platinum containing chemotherapy for treatment of primary tumor in adjuvant, locally advanced, or metastatic settings, or is intolerant, or refused such treatment. May have received prior immunotherapy. There is no limit on lines of prior anti-cancer therapies.

(b) Histologically or cytologically confirmed diagnosis of advanced NSCLC (stage IIIB or IV) or recurrent disease. Has squamous cell, adenosquamous or large cell carcinoma. Has received at least one prior systemic therapy. Subjects whose tumors are known to have EGFR mutations or ALK gene rearrangements have failed (progressive disease or unacceptable toxicity) prior EGFR inhibitor or ALK tyrosine kinase inhibitor, respectively. Subjects with ROS-1 positive tumors have failed an ALK inhibitor (crizotinib). May have received PD-1 inhibitors. There is no limit on lines of prior anti-cancer therapies.

Exclusion of subjects is based primarily on HLA-A genotype ie if: Subject is HLA-A*02:05 positive. Subject has HLA-A*02:07 as the sole HLA-A*02 allele (eg. A subject with HLA alleles A*02:04 and A*02:07 is eligible). Subject has any A*02 null allele (designated with an "N", eg, A*-2: 32N) as the sole HLA-A*02 allele. Excluded subjects include those with symptomatic CNS metastases.

Following leukapheresis the cells are subsequently transduced with the MAGE-A4$^{c1032}$T cells (SEQ ID NO: 5, 7) specific for MAGE-A4 antigen (particularly the specific MAGE-A4 antigenic peptide SEQ ID NO:2) and the cells expanded and cryopreserved for later use. Once the MAGE-A4$^{c1032}$T cells were available, subjects underwent lymphodepleting chemotherapy with cyclophosphamide plus fludarabine on Days −7 to −5, or Days −7 to −4 followed by infusion of transduced cells on Day 1.

Three subject cohorts were treated dosing with between 100 million to 5 billion transduced cells respectively with no dose escalation:

100 mn cell dose, (cyclophosphamide: 500 mg/m$^2$/d)×3d; (fludarabine: 20 mg/m$^2$/d)×3d 1bn cell dose, (cyclophosphamide: 500 mg/m$^2$/d)×3d; (fludarabine: 20 mg/m$^2$/d)×3d 5bn cell dose, (cyclophosphamide: 600 mg/m$^2$/d)×3d; (fludarabine: 30 mg/m$^2$/d)×4d Subjects are hospitalised for 7 days following infusion and monitored for safety, T-cell persistence, cytokine production with CT and MRI performed at weeks 4, 8, 16, 24 and 3 monthly thereafter until disease progression or early interventional withdrawal, long term follow up annually is planned for a 15 year period.

A subject will be considered completing the interventional phase of the study when he/she has received T-cell infusion and then progressed or died prior to disease progression. Optionally a second T-cell infusion may be given, and they will remain in the interventional phase of the study until they have further progression of disease. Once progression is established, no further efficacy assessments are performed other than overall survival. All subjects completing from the interventional portion of the study will enter the long-term follow-up (LTFU) phase for observation of delayed adverse events (AEs) during the 15 years post-infusion in accordance with FDA and EMA regulations. This study will be considered complete when the last living subject has completed LTFU.

To evaluate the safety and tolerability of MAGE-A4$^{c1032}$T the incidence of dose limiting toxicities (DLTs) is monitored, determination is made of optimally tolerated dose range, adverse events (AEs), and Serious Adverse Events (SAEs); laboratory assessments, including chemistry, haematology, and coagulation; and cardiac assessments, including ECG and cardiac Troponin.

During the study MAGE-A4 is evaluated as a biomarker for tumour MAGE-A4 expression, and antitumor activity. This is performed to correlate the level of antigen expression in tumour level at Baseline, and post MAGE-A4$^{c1032}$T cell infusion. Post-therapy MAGE-A4 expression in tumour over time is assessed to determine tumour immunity or resistance to MAGE-A4$^{c1032}$T. Additionally, circulating cytokines were measured and evaluated for association with cytokine release syndrome (CRS) and other adverse events (AEs). Additionally post MAGE-A4$^{c1032}$T cell infusion, transduced cell persistence is assessed by determination of serum level persistence of MAGE-A4$^{c1032}$T engineered T-cell as measured by MAGE-A4$^{c1032}$T vector copy number and MAGE-A4$^{c1032}$T transduced T-cell number. Mean expression of specific surface markers on gene-modified T cells in subject blood and tumour were measured by fluorescence intensity. Killing profile and cytokine profile of genetically modified T cells were evaluated using flow cytometry in blood and tumor.

Biomarkers of subject sample including polymorphisms in cytokine genes and cytokine production.

To evaluate anti-tumour activity of MAGE-A4$^{c1032}$T the following endpoints are monitored by RECIST v1.1; Overall Response Rate (ORR) defined as the proportion of subjects with a confirmed complete response (CR) or partial response (PR). Additional endpoints are monitored for duration of response (DoR), duration of stable disease (SD), progression free survival (PFS), overall survival (OS). Evaluation was made of the efficacy of the treatment by assessment of duration of response and assessment of overall survival. Also assessed were intervals for (a) the date of first T cell infusion dose and first documented evidence of CR or PR and evaluation of the efficacy of the treatment by assessment of time to first response.
(b) the date of first documented evidence of CR or PR until first documented disease progression or death due to any cause.
(c) the date of first documented evidence of stable disease (SD) until first documented disease progression or death due to any cause.
(d) the date of first T cell infusion and the earliest date of disease, progression or death due to any cause.
(e) between the date of first T cell infusion and date of death due to any cause.

Evaluation of the efficacy of the treatment by Number and % of subjects having any Long Term Follow Up Adverse Events (AEs), malignancy, neurologic disorder, rheumatologic or other autoimmune disorder, hematologic disorder, infections Subjects were additionally monitored for safety and tolerability response through laboratory assessments including chemistry, hematology and coagulation, and anti-MAGE-A4 TCR antibodies, adverse events (AE), including serious adverse events (SAEs), dose limiting toxicities (DLT) NCI CTCAE and optimally tolerated dose range and evaluation of persistence of genetically modified T cells in the periphery and retention of heterologous TCR expression in the T cells PBMCs using PCR-based assay.

The same study was also extended to investigate treatment of subjects with ovarian cancer, melanoma and urothelial/bladder cancer and sarcoma (synovial sarcoma) with MAGE-A4$^{c1032}$T for which data is presented below.

Results

Data presented in FIG. 1 provide the best overall response defined as the best response recorded from the date of T cell infusion until disease progression based on RECIST v1.1 criteria for responses in, head & neck cancer, and lung cancer for patients receiving a MAGE-A4$^{c1032}$ T-cell infusion cell dose of between 5×10$^9$ and 10×10$^9$ cells (5 to 10 bn cells). These data support confirmed responses seen in subjects with head and neck cancer and lung cancer.

The data in FIG. 2 represent the CT scans of 42-yr-old male subject diagnosed age 25 and recently developed metastatic disease. The subject had moderate MAGE-A4 expression at baseline (16% 1+, 37% 2+, 41% 3+) and large disease burden; baseline SLD was 20 cm and was provided a first infusion of ~10 billion SPEAR MAGE-A4$^{c1032}$ T-cells, adverse reaction was minimal developing grade 2 CRS (cytokine release syndrome) and cytopenias and consistent with those typically experienced by cancer patients undergoing cytotoxic chemotherapy and/or cancer immunotherapy. For lung cancer the tumour showed a greater than 45% decrease by RECIST 1.1 and symptoms of shortness of breath were resolved by treatment. The shortness of breath was due to fluid in pleural space, FIG. 2 lower left, seen resolved in lower right. FIG. 2 also shows a massive tumor displacing major blood vessels and compressing the right lung at baseline, upper left panel, and twelve weeks following treatment the tumor is dramatically decreased and non-target lesion absent, top right scan. FIG. 2 bottom right scan shows the lung expanded.

Data in FIG. 3 show the tumour responses for cohort subjects with different MAGE-A4 expressing cancers and the percent changes in sum of diameters in target lesions over a measured period of weeks as indicated following the date of T cell infusion. The data confirms the 24 week or 6 month efficacy of response in terms of tumour size reduction (36% reduction) for head and neck cancer treatment.

Data for ovarian cancer, urothelial/bladder cancer, and melanoma individual subjects also demonstrated a reduction in tumour size following treatment with MAGE-A4$^{c1032}$ T-cell (between 5 to 10bn cell infusion) as determined by percentage changes in sum of diameters in target lesions based on the (SLD) sum of the long diameters for non-nodal lesions and short axis for nodal lesions; responses were evaluated by RECIST 1.1. Data demonstrated tumour SLD reductions of about 9% reduction for ovarian cancer at 12 weeks post infusion of MAGE-A4$^{c1032}$T engineered T-cells, about 21% reduction for melanoma at 6 weeks post infusion of MAGE-A4$^{c1032}$T engineered T-cells, approximately 67% reduction for urothelial/bladder cancer at 6 weeks post infusion of MAGE-A4$^{c1032}$T engineered T-cells (FIG. 3). The data therefore demonstrates therapeutic efficacy and target tumor reductions observed in patients with ovarian, urothelial/bladder, and melanoma cancers.

In conclusion the data from the clinical studies show a confirmed response seen in subjects with head and neck cancer and lung cancer with tumor reductions also observed in patients with ovarian, bladder, and melanoma.

Sequences

SEQ ID NO: 1, MAGE A4

```
MSSEQKSQHC KPEEGVEAQE EALGLVGAQA PTTEEQEAAV
SSSSPLVPGT LEEVPAAESA GPPQSPQGAS ALPTTISFTC
WRQPNEGSSS QEEEGPSTSP DAESLFREAL SNKVDELAHF
LLRKYRAKEL VIKAEMLERV IKNYKRCFPV IFGKASESLK
MIFGIDVKEV DPASNTYTLV TCLGLSYDGL LGNNQIFPKT
GLLIIVLGTI AMEGDSASEE EIWEELGVMG VYDGREHTVY
GEPRELLTQD WVQENYLEYR QVPGSNPARY EFLWGPRALA
ETSYVKVLEH VVRVNARVRI AYPSLREAAL LEEEEGV
```

SEQ ID NO: 2, MAGE A4 Peptide

GVYDGREHTV

SEQ ID NO: 3; (CD8x) CDRs bold underlined, signal sequence italic underlined

*MALPVTALLLPLALLLHAAR*PSQFRVSPLDRTWNLGETVELKCQVLLSNPTSGCSWLFQPRGAAASPT

FLLYLSQNKPKAAEGLDTQRFSGKRLGDTFVLTLSDERRENEGYYFCSALSNSIMYFSHFVPVFLPAK

PTTTPAPRPPTPAPTIASQPLSLRPEACRPAAGGAVHTRGLDFACDIYIWAPLAGTCGVLLLSLVITL

YCNHRNRRRVCKCPRPVVKSGDKPSLSARYV

SEQ ID NO: 4; (CD8α)

ATGGCCTTACCAGTGACCGCCTTGCTCCTGCCGCTGGCCTTGCTGCTCCACGCCGCCAGGCCGAGCCA

GTTCCGGGTGTCGCCGCTGGATCGGACCTGGAACCTGGGCGAGACAGTGGAGCTGAAGTGCCAGGTGC

TGCTGTCCAACCCGACGTCGGGCTGCTCGTGGCTCTTCCAGCCGCGCGGCGCCGCCGCCAGTCCCACC

TTCCTCCTATACCTCTCCCAAAACAAGCCCAAGGCGGCCGAGGGGCTGGACACCCAGCGGTTCTCGGG

CAAGAGGTTGGGGGACACCTTCGTCCTCACCCTGAGCGACTTCCGCCGAGAGAACGAGGGCTACTATT

TCTGCTCGGCCCTGAGCAACTCCATCATGTACTTCAGCCACTTCGTGCCGGTCTTCCTGCCAGCGAAG

CCCACCACGACGCCAGCGCCGCGACCACCAACACCGGCGCCCACCATCGCGTCGCAGCCCCTGTCCCT

GCGCCCAGAGGCGTGCCGGCCAGCGGGGGGGGCGCAGTGCACACGAGGGGGCTGGACTTCGCCTGTG

ATATCTACATCTGGGCGCCCTTGGCCGGGACTTGTGGGGTCCTTCTCCTGTCACTGGTTATCACCCTT

TACTGCAACCACAGGAACCGAAGACGTGTTTGCAAATGTCCCCGGCCTGTGGTCAAATCGGGAGACAA

GCCCAGCCTTTCGGCGAGATACGTCGGTTCAAGAGCTAAAAGAAGTGGTAGTGGTGCCCCTGTGA

SEQ ID NO: 5; (MAGE A4 TCR α chain) CDRs bold underlined

MKKHLTTFLVILWLYFYRGNGKNQVEQSPQSLIILEGKNCTLQCNYTVSPFSNLRWYKQDTGRGPVSL

TILTFSENTKSNGRYTATLDADTKQSSLHITASQLSDSASYICVVSGGTDSWGKLQFGAGTQVVVTPD

IQNPDPAVYQLRDSKSSDKSVCLFTDFDSQTNVSQSKDSDVYITDKTVLDMRSMDFKSNSAVAWSNKS

DFACANAFNNSIIPEDTFFPSPESSCDVKLVEKSFETDINLNFQNLSVIGFRILLLKVAGENLLMTLR

LWSSGSRAKR

SEQ ID NO: 6; (MAGE A4 TCR α chain coding sequence)

ATGAAGAAGCACCTGACCACCTTTCTCGTGATCCTGTGGCTGTACTTCTACCGGGGCAACGGCAAGAA

CCAGGTGGAACAGAGCCCCCAGAGCCTGATCATCCTGGAAGGCAAGAACTGCACCCTGCAGTGCAACT

ACACCGTGTCCCCCTTCAGCAACCTGCGGTGGTACAAGCAGGACACCGGCAGAGGCCCTGTGTCCCTG

ACCATCCTGACCTTCAGCGAGAACACCAAGAGCAACGGCCGGTACACCGCCACCCTGGACGCCGATAC

-continued

AAAGCAGAGCAGCCTGCACATCACCGCCAGCCAGCTGAGCGATAGCGCCAGCTACATCTGCGTGGTGT

CCGGCGGCACAGACAGCTGGGGCAAGCTGCAGTTTGGCGCCGGAACACAGGTGGTCGTGACCCCCGAC

ATCCAGAACCCTGACCCTGCCGTGTACCAGCTGCGGGACAGCAAGAGCAGCGACAAGAGCGTGTGCCT

GTTCACCGACTTCGACAGCCAGACCAACGTGTCCCAGAGCAAGGACAGCGACGTGTACATCACCGACA

AGACCGTGCTGGACATGCGGAGCATGGACTTCAAGAGCAATAGCGCCGTGGCCTGGTCCAACAAGAGC

GACTTCGCCTGCGCCAACGCCTTCAACAACAGCATTATCCCCGAGGACACATTCTTCCCAAGCCCCGA

GAGCAGCTGCGACGTCAAGCTGGTGGAAAAGAGCTTCGAGACAGACACCAACCTGAACTTCCAGAACC

TGAGCGTGATCGGCTTCAGAATCCTGCTGCTGAAGGTGGCCGGCTTCAACCTGCTGATGACCCTGAGA

CTGTGGTCCAGCGGCAGCCGGGCCAAGAGA

SEQ ID NO: 7; (MAGE A4 TCR β chain) CDRs bold underlined
MASLLFFCGAFYLLGTGSMDADVTQTPRNRITKTGKRIMLECSQTKGHDRMYWYRQDPGLGLRLIYYS

FDVKDINKGEISDGYSVSRQAQAKFSLSLESAIPNQTALYFCATSGQGAYEEQFFGPGTRLTVLEDLK

NVFPPEVAVFEPSEAEISHTQKATLVCLATGFYPDHVELSWWVNGKEVHSGVSTDPQPLKEQPALNDS

RYCLSSRLRVSATFWQNPRNHERCQVQFYGLSENDEWTQDRAKPVTQIVSAEAWGRADCGFTSESYQQ

GVLSATILYEILLGKATLYAVLVSALVLMAMVKRKDSRG

SEQ ID NO: 8; (MAGE A4 TCR β chain coding sequence)
ATGGCCAGCCTGCTGTTCTTCTGCGGCGCCTTCTACCTGCTGGGCACCGGCTCTATGGATGCCGACGT

GACCCAGACCCCCCGGAACAGAATCACCAAGACCGGCAAGCGGATCATGCTGGAATGCTCCCAGACCA

AGGGCCACGACCGGATGTACTGGTACAGACAGGACCCTGGCCTGGGCCTGCGGCTGATCTACTACAGC

TTCGACGTGAAGGACATCAACAAGGGCGAGATCAGCGACGGCTACAGCGTGTCCAGACAGGCTCAGGC

CAAGTTCAGCCTGTCCCTGGAAAGCGCCATCCCCAACCAGACCGCCCTGTACTTTTGTGCCACAAGCG

GCCAGGGCGCCTACGAGGAGCAGTTCTTTGGCCCTGGCACCCGGCTGACAGTGCTGGAAGATCTGAAG

AACGTGTTCCCCCCAGAGGTGGCCGTGTTCGAGCCTTCTGAGGCCGAAATCAGCCACACCCAGAAAGC

CACACTCGTGTGTCTGGCCACCGGCTTCTACCCCGACCACGTGGAACTGTCTTGGTGGGTCAACGGCA

AAGAGGTGCACAGCGGCGTGTCCACCGATCCCCAGCCTCTGAAAGAACAGCCCGCCCTGAACGACAGC

CGGTACTGCCTGAGCAGCAGACTGAGAGTGTCCGCCACCTTCTGGCAGAACCCCAGAAACCACTTCAG

ATGCCAGGTGCAGITTTACGGCCTGAGCGAGAACGACGAGTGGACCCAGGACAGAGCCAAGCCCGTGA

CACAGATCGTGTCTGCCGAAGCTTGGGGGCGCGCCGATTGTGGCTTTACCAGCGAGAGCTACCAGCAG

GGCGTGCTGAGCGCCACCATCCTGTACGAGATCCTGCTGGGAAAGGCCACACTGTACGCCGTGCTGGT

GTCTGCCCTGGTGCTGATGGCCATGGTCAAGCGGAAGGACAGCCGGGGC

SEQ ID NO: 9; (MAGE A4 TCR α chain variable region) 136AA - CDRs bold underlined
MKKHLTTFLVILWLYFYRGNGKNQVEQSPQSLIILEGKNCTLQCNYTVSPFSNLRWYKQDTGRGPVSL

TILTFSENTKSNGRYTATLDADTKQSSLHITASQLSDSASYICVVSGGTDSWGKLQFGAGTQVVVTPD

SEQ ID NO: 10; (MAGE A4 TCR β chain variable region) 133AA - CDRs bold underlined
MASLLFFCGAFYLLGTGSMDADVTQTPRNRITKTGKRIMLECSQTKGHDRMYWYRQDPGLGLRLIYYS

FDVKDINKGEISDGYSVSRQAQAKFSLSLESAIPNQTALYFCATSGQGAYEEQFFGPGIRLTVLE

SEQ ID NO: 11; CDR1 MAGE A4 TCR α chain, (residues 48-53)
VSPFSN

SEQ ID NO: 12; CDR2 MAGE A4 TCR α chain, (residues 71-76)
LTFSEN

SEQ ID NO: 13; CDR3 MAGE A4 TCR α chain, (residues 111-125)
CVVSGGTDSWGKLQF

SEQ ID NO: 14; CDR1 MAGE A4 TCR β chain, (residues 46-50)
KGHDR

SEQ ID NO: 15; CDR2 MAGE A4 TCR β chain, (residues 68-73)
SFDVKD

SEQ ID NO: 16; CDR3 MAGE A4 TCR β chain, (residues 110-123)
CATSGQGAYEEQFF

SEQ ID NO: 17; CDR1 CD8α (residues 45-53)
VLLSNPTSG

SEQ ID NO: 18; CDR2 CD8α (residues 72-79)
YLSQNKPK

SEQ ID NO: 19; CDR3 CD8α (residues 118-123)
LSNSIM

The invention claimed is:

1. A method of treating, preventing progression of, or delaying progression of synovial sarcoma in a subject, the method consisting of administering to the subject an effective amount of modified immunoresponsive cells presenting a heterologous T-cell receptor (TCR), the heterologous TCR comprising:

(i) a TCR alpha chain variable domain comprising:

a complementarity determining region 1 (αCDR1) comprising the amino acid sequence VSPFSN (SEQ ID NO:11);

a complementarity determining region 2 (αCDR2) comprising the amino acid sequence LTFSEN (SEQ ID NO:12); and a complementarity determining region 3 (αCDR3) comprising the amino acid sequence CVVSGGTDSWGKLQF (SEQ ID NO:13); and (ii) a TCR beta chain variable domain comprising:

a complementarity determining region 1 (βCDR1) comprising the amino acid sequence KGHDR (SEQ ID NO:14);

a complementarity determining region 2 (βCDR2) comprising the amino acid sequence SFDVKD (SEQ ID NO:15); and a complementarity determining region 3 (βCDR3) comprising the amino acid sequence CATSGQGAYEEQFF (SEQ ID NO:16);

wherein the synovial sarcoma expresses a peptide antigen of melanoma-associated antigen A4 (MAGE-A4) comprising the amino acid sequence GVYDGREHTV (SEQ ID NO: 2); and wherein the modified immunoresponsive cells do not express or present a heterologous CD8 co-receptor.

2. The method according to claim 1, wherein the peptide antigen of MAGE-A4 is complexed with a peptide presenting molecule selected from the group consisting of a major histocompatibility complex (MHC) and a human leukocyte antigen (HLA).

3. The method according to claim 2, wherein the peptide presenting molecule is selected from the group consisting of HLA-A*02, HLA-A*02:01, HLA-A*02:02, HLA-A*02:03, HLA-A*02:04, HLA-A*02:06, HLA-A*02:642, and HLA-A*02:07.

4. The method according to claim 3, wherein the peptide presenting molecule is selected from the group consisting of HLA-A*02:01, HLA-A*02:02, HLA-A*02:03, and HLA-A*02:06.

5. The method according to claim 1, wherein the heterologous TCR comprises an amino acid sequence that has at least 80%, identity to the alpha chain variable domain of SEQ ID NO: 9.

6. The method according to claim 1, wherein the heterologous TCR comprises an amino acid sequence that has at least 80% identity to the beta chain variable domain of SEQ ID NO: 10.

7. The method according to claim 1, wherein the heterologous TCR comprises an amino acid sequence comprising the alpha chain variable domain of SEQ ID NO: 9 and wherein the beta chain variable domain comprises an amino acid sequence comprising the beta chain variable domain of SEQ ID NO: 10.

8. The method according to claim 1, wherein the heterologous TCR comprises an amino acid sequence that has at least 80% identity to the alpha chain of SEQ ID NO: 5.

9. The method according to claim 1, wherein the heterologous TCR comprises an amino acid sequence that has at least 80% identity to the beta chain of SEQ ID NO: 7.

10. The method according to claim 1, wherein the heterologous TCR comprises an amino acid sequence comprising the alpha chain of SEQ ID NO: 5 and an amino acid sequence comprising the beta chain of SEQ ID NO: 7.

11. The method according to claim 1, wherein the modified immunoresponsive cells are B cells, T cells, or natural killer cells.

12. The method according to claim 1, wherein the modified immunoresponsive cells are CD4+ T cells, CD8+ T cells, or a mixed population of CD4+ T cells and CD8+ T cells.

13. The method according to claim 12, wherein the modified immunoresponsive cells are a mixed population of CD4+ T cells and CD8+ T cells.

14. The method according to claim 1, wherein the synovial sarcoma is metastatic or non-resectable.

15. The method according to claim 1, wherein the subject is intolerant to a standard of care treatment or wherein the synovial sarcoma has been previously unsuccessfully treated with surgery, radiation therapy, targeted therapy, immunotherapy, chemotherapy, or a combination thereof.

16. The method according to claim 15, wherein the synovial sarcoma has been previously unsuccessfully treated with chemotherapy.

17. The method according to claim 1, wherein the modified immunoresponsive cells are administered at a dose of between about 500 million to about 10 billion cells.

18. The method according to claim 1, wherein the modified immunoresponsive cells are administered at a dose of between: about 500 million to about 1 billion cells, or about 2 billion to about 5 billion cells, or about 6 billion to about 10 billion cells.

19. The method according to claim 1, wherein the modified immunoresponsive cells are administered as:

(a) a single dose in each of one or more dosing cycles, (b) one or more doses in each of one or more dosing cycles, (c) a single dose on the first day of each of one or more dosing cycles, (d) one or more doses in each of one or more dosing cycles, at least one dose being on the first day of each cycle, (e) one or more doses in each of one or more dosing cycles, at least one dose being on the first day of each cycle, or (f) a single dose.

20. The method according to claim 1, wherein the subject undergoes lymphodepleting chemotherapy prior to administration of the modified immunoresponsive cells.

21. The method according to claim 20, wherein the lymphodepleting chemotherapy comprises: (i) administration of fludarabine for four days, starting on the seventh day prior to administration of the modified immunoresponsive cells; and (ii) administration of cyclophosphamide for three days starting on the seventh day prior to administration of the modified immunoresponsive cells.

* * * * *

SEQUENCE LISTING

```
<160> NUMBER OF SEQ ID NOS: 19

<210> SEQ ID NO 1
<211> LENGTH: 317
<212> TYPE: PRT
<213> ORGANISM: Homo sapiens

<400> SEQUENCE: 1

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
        115                 120                 125

Glu Leu Val Thr Lys Ala Glu Met Leu Glu Arg Val Ile Lys Asn Tyr
    130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly
        195                 200                 205

Thr Ile Ala Met Glu Gly Asp Ser Ala Ser Glu Glu Glu Ile Trp Glu
    210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
            260                 265                 270

Leu Trp Gly Pro Arg Ala Leu Ala Glu Thr Ser Tyr Val Lys Val Leu
        275                 280                 285
```

Glu His Val Val Arg Val Asn Ala Arg Val Arg Ile Ala Tyr Pro Ser
290 295 300

Leu Arg Glu Ala Ala Leu Leu Glu Glu Glu Glu Gly Val
305 310 315

<210> SEQ ID NO 2
<211> LENGTH: 10
<212> TYPE: PRT
<213> ORGANISM: Homo sapiens

<400> SEQUENCE: 2

Gly Val Tyr Asp Gly Arg Glu His Thr Val
1 5 10

<210> SEQ ID NO 3
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Met Ala Leu Pro Val Thr Ala Leu Leu Leu Pro Leu Ala Leu Leu Leu
1 5 10 15

His Ala Ala Arg Pro Ser Gln Phe Arg Val Ser Pro Leu Asp Arg Thr
20 25 30

Trp Asn Leu Gly Glu Thr Val Glu Leu Lys Cys Gln Val Leu Leu Ser
35 40 45

Asn Pro Thr Ser Gly Cys Ser Trp Leu Phe Gln Pro Arg Gly Ala Ala
50 55 60

Ala Ser Pro Thr Phe Leu Leu Tyr Leu Ser Gln Asn Lys Pro Lys Ala
65 70 75 80

Ala Glu Gly Leu Asp Thr Gln Arg Phe Ser Gly Lys Arg Leu Gly Asp
85 90 95

Thr Phe Val Leu Thr Leu Ser Asp Phe Arg Arg Glu Asn Glu Gly Tyr
100 105 110

Tyr Phe Cys Ser Ala Leu Ser Asn Ser Ile Met Tyr Phe Ser His Phe
115 120 125

Val Pro Val Phe Leu Pro Ala Lys Pro Thr Thr Thr Pro Ala Pro Arg
130 135 140

Pro Pro Thr Pro Ala Pro Thr Ile Ala Ser Gln Pro Leu Ser Leu Arg
145 150 155 160

Pro Glu Ala Cys Arg Pro Ala Ala Gly Gly Ala Val His Thr Arg Gly
165 170 175

Leu Asp Phe Ala Cys Asp Ile Tyr Ile Trp Ala Pro Leu Ala Gly Thr
180 185 190

Cys Gly Val Leu Leu Leu Ser Leu Val Ile Thr Leu Tyr Cys Asn His
195 200 205

Arg Asn Arg Arg Arg Val Cys Lys Cys Pro Arg Pro Val Val Lys Ser
210 215 220

Gly Asp Lys Pro Ser Leu Ser Ala Arg Tyr Val
225 230 235

<210> SEQ ID NO 4
<211> LENGTH: 745
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4
atggccttac cagtgaccgc cttgctcctg ccgctggcct tgctgctcca cgccgccagg 60
ccgagccagt tccgggtgtc gccgctggat cggacctgga acctgggcga gacagtggag 120
ctgaagtgcc aggtgctgct gtccaacccg acgtcgggct gctcgtggct cttccagccg 180
cgcggcgccg ccgccagtcc caccttcctc ctatacctct cccaaaacaa gcccaaggcg 240
gccgaggggc tggacaccca gcggttctcg ggcaagaggt tgggggacac cttcgtcctc 300
accctgagcg acttccgccg agagaacgag ggctactatt tctgctcggc cctgagcaac 360
tccatcatgt acttcagcca cttcgtgccg gtcttcctgc cagcgaagcc caccacgacg 420
ccagcgccgc gaccaccaac accggcgccc accatcgcgt cgcagcccct gtccctgcgc 480
ccagaggcgt gccggccagc ggcggggggc gcagtgcaca cgagggggct ggacttcgcc 540
tgtgatatct acatctgggc gcccttggcc gggacttgtg gggtccttct cctgtcactg 600
gttatcaccc tttactgcaa ccacaggaac cgaagacgtg tttgcaaatg tccccggcct 660
gtggtcaaat cgggagacaa gcccagcctt tcggcgagat acgtcggttc aagagctaaa 720
agaagtggta gtggtgcccc tgtga 745

<210> SEQ ID NO 5
<211> LENGTH: 282
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

Met Lys Lys His Leu Thr Thr Phe Leu Val Ile Leu Trp Leu Tyr Phe
1 5 10 15

Tyr Arg Gly Asn Gly Lys Asn Gln Val Glu Gln Ser Pro Gln Ser Leu
20 25 30

Ile Ile Leu Glu Gly Lys Asn Cys Thr Leu Gln Cys Asn Tyr Thr Val
35 40 45

Ser Pro Phe Ser Asn Leu Arg Trp Tyr Lys Gln Asp Thr Gly Arg Gly
50 55 60

Pro Val Ser Leu Thr Ile Leu Thr Phe Ser Glu Asn Thr Lys Ser Asn
65 70 75 80

Gly Arg Tyr Thr Ala Thr Leu Asp Ala Asp Thr Lys Gln Ser Ser Leu
85 90 95

His Ile Thr Ala Ser Gln Leu Ser Asp Ser Ala Ser Tyr Ile Cys Val
100 105 110

Val Ser Gly Gly Thr Asp Ser Trp Gly Lys Leu Gln Phe Gly Ala Gly
115 120 125

Thr Gln Val Val Val Thr Pro Asp Ile Gln Asn Pro Asp Pro Ala Val
130 135 140

Tyr Gln Leu Arg Asp Ser Lys Ser Ser Asp Lys Ser Val Cys Leu Phe
145 150 155 160

Thr Asp Phe Asp Ser Gln Thr Asn Val Ser Gln Ser Lys Asp Ser Asp
165 170 175

```
Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
        195                 200                 205

Ala Asn Ala Phe Asn Asn Ser Ile Ile Pro Glu Asp Thr Phe Phe Pro
    210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser Gly Ser Arg Ala Lys Arg
        275                 280
```

<210> SEQ ID NO 6
<211> LENGTH: 846
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
atgaagaagc acctgaccac ctttctcgtg atcctgtggc tgtacttcta ccggggcaac     60

ggcaagaacc aggtggaaca gagcccccag agcctgatca tcctggaagg caagaactgc    120

accctgcagt gcaactacac cgtgtccccc ttcagcaacc tgcggtggta caagcaggac    180

accggcagag gccctgtgtc cctgaccatc ctgaccttca gcgagaacac caagagcaac    240

ggccggtaca ccgccaccct ggacgccgat acaaagcaga gcagcctgca catcaccgcc    300

agccagctga gcgatagcgc cagctacatc tgcgtggtgt ccggcggcac agacagctgg    360

ggcaagctgc agtttggcgc cggaacacag gtggtcgtga cccccgacat ccagaaccct    420

gaccctgccg tgtaccagct gcgggacagc aagagcagcg acaagagcgt gtgcctgttc    480

accgacttcg acagccagac caacgtgtcc cagagcaagg acagcgacgt gtacatcacc    540

gacaagaccg tgctggacat gcggagcatg gacttcaaga gcaatagcgc cgtggcctgg    600

tccaacaaga gcgacttcgc ctgcgccaac gccttcaaca acagcattat ccccgaggac    660

acattcttcc caagccccga gagcagctgc gacgtcaagc tggtggaaaa gagcttcgag    720

acagacacca acctgaactt ccagaacctg agcgtgatcg gcttcagaat cctgctgctg    780

aaggtggccg gcttcaacct gctgatgacc ctgagactgt ggtccagcgg cagccgggcc    840

aagaga                                                                846
```

<210> SEQ ID NO 7
<211> LENGTH: 311
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
```

```
            20                  25                  30

Lys Thr Gly Lys Arg Ile Met Leu Glu Cys Ser Gln Thr Lys Gly His
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Gly Gln Gly Ala Tyr Glu Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310
```

<210> SEQ ID NO 8
<211> LENGTH: 933
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
atggccagcc tgctgttctt ctgcggcgcc ttctacctgc tgggcaccgg ctctatggat      60

gccgacgtga cccagacccc ccggaacaga atcaccaaga ccggcaagcg gatcatgctg     120

gaatgctccc agaccaaggg ccacgaccgg atgtactggt acagacagga ccctggcctg     180

ggcctgcggc tgatctacta cagcttcgac gtgaaggaca tcaacaaggg cgagatcagc     240

gacggctaca gcgtgtccag acaggctcag gccaagttca gcctgtccct ggaaagcgcc     300

atccccaacc agaccgccct gtacttttgt gccacaagcg gccagggcgc ctacgaggag     360
```

```
cagttctttg gccctggcac ccggctgaca gtgctggaag atctgaagaa cgtgttcccc    420

ccagaggtgg ccgtgttcga gccttctgag gccgaaatca gccacaccca gaaagccaca    480

ctcgtgtgtc tggccaccgg cttctacccc gaccacgtgg aactgtcttg gtgggtcaac    540

ggcaaagagg tgcacagcgg cgtgtccacc gatccccagc ctctgaaaga acagcccgcc    600

ctgaacgaca gccggtactg cctgagcagc agactgagag tgtccgccac cttctggcag    660

aaccccagaa accacttcag atgccaggtg cagttttacg gcctgagcga gaacgacgag    720

tggacccagg acagagccaa gcccgtgaca cagatcgtgt ctgccgaagc ttgggggcgc    780

gccgattgtg gctttaccag cgagagctac cagcagggcg tgctgagcgc caccatcctg    840

tacgagatcc tgctgggaaa ggccacactg tacgccgtgc tggtgtctgc cctggtgctg    900

atggccatgg tcaagcggaa ggacagccgg ggc                                 933
```

<210> SEQ ID NO 9
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Met Lys Lys His Leu Thr Thr Phe Leu Val Ile Leu Trp Leu Tyr Phe
1               5                   10                  15

Tyr Arg Gly Asn Gly Lys Asn Gln Val Glu Gln Ser Pro Gln Ser Leu
            20                  25                  30

Ile Ile Leu Glu Gly Lys Asn Cys Thr Leu Gln Cys Asn Tyr Thr Val
        35                  40                  45

Ser Pro Phe Ser Asn Leu Arg Trp Tyr Lys Gln Asp Thr Gly Arg Gly
    50                  55                  60

Pro Val Ser Leu Thr Ile Leu Thr Phe Ser Glu Asn Thr Lys Ser Asn
65                  70                  75                  80

Gly Arg Tyr Thr Ala Thr Leu Asp Ala Asp Thr Lys Gln Ser Ser Leu
                85                  90                  95

His Ile Thr Ala Ser Gln Leu Ser Asp Ser Ala Ser Tyr Ile Cys Val
            100                 105                 110

Val Ser Gly Gly Thr Asp Ser Trp Gly Lys Leu Gln Phe Gly Ala Gly
        115                 120                 125

Thr Gln Val Val Val Thr Pro Asp
    130                 135
```

<210> SEQ ID NO 10
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
```

```
        35                  40                  45

Asp Arg Met Tyr Trp Tyr Arg Gln Asp Pro Gly Leu Gly Leu Arg Leu
    50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Gly Gln Gly Ala Tyr Glu Glu Gln Phe Phe Gly Pro Gly Thr Arg
        115                 120                 125

Leu Thr Val Leu Glu
    130


<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Ser Pro Phe Ser Asn
1               5


<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Thr Phe Ser Glu Asn
1               5


<210> SEQ ID NO 13
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Cys Val Val Ser Gly Gly Thr Asp Ser Trp Gly Lys Leu Gln Phe
1               5                   10                  15


<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Gly His Asp Arg
1               5
```

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

Ser Phe Asp Val Lys Asp
1 5

<210> SEQ ID NO 16
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Cys Ala Thr Ser Gly Gln Gly Ala Tyr Glu Glu Gln Phe Phe
1 5 10

<210> SEQ ID NO 17
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Val Leu Leu Ser Asn Pro Thr Ser Gly
1 5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Tyr Leu Ser Gln Asn Lys Pro Lys
1 5

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Leu Ser Asn Ser Ile Met
1 5